United States Patent
deLong et al.

(10) Patent No.: US 9,096,569 B2
(45) Date of Patent: *Aug. 4, 2015

(54) BETA- AND GAMMA-AMINO-ISOQUINOLINE AMIDE COMPOUNDS AND SUBSTITUTED BENZAMIDE COMPOUNDS

(71) Applicant: Aerie Pharmaceuticals, Inc., Research Triangle Park, NC (US)

(72) Inventors: Mitchell A. deLong, Chapel Hill, NC (US); Jill Marie Sturdivant, Chapel Hill, NC (US); Susan M. Royalty, Davis, CA (US)

(73) Assignee: Aerie Pharmaceuticals, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/273,895

(22) Filed: May 9, 2014

(65) Prior Publication Data

US 2014/0249201 A1     Sep. 4, 2014

Related U.S. Application Data

(60) Continuation of application No. 13/442,263, filed on Apr. 9, 2012, now Pat. No. 8,759,388, which is a division of application No. 12/180,259, filed on Jul. 25, 2008, now Pat. No. 8,450,344.

(51) Int. Cl.
| | |
|---|---|
| *A61K 31/47* | (2006.01) |
| *A61K 31/4709* | (2006.01) |
| *C07D 215/38* | (2006.01) |
| *C07D 401/02* | (2006.01) |
| *C07D 409/02* | (2006.01) |
| *C07D 333/24* | (2006.01) |
| *A61K 31/381* | (2006.01) |
| *A61K 31/16* | (2006.01) |
| *C07D 217/02* | (2006.01) |
| *C07D 217/24* | (2006.01) |
| *C07D 401/12* | (2006.01) |
| *C07D 405/12* | (2006.01) |
| *C07D 409/12* | (2006.01) |
| *C07D 413/12* | (2006.01) |
| *C07D 417/12* | (2006.01) |
| *C07C 237/04* | (2006.01) |

(52) U.S. Cl.
CPC .............. *C07D 333/24* (2013.01); *A61K 31/16* (2013.01); *A61K 31/381* (2013.01); *A61K 31/47* (2013.01); *A61K 31/4709* (2013.01); *C07C 237/04* (2013.01); *C07D 217/02* (2013.01); *C07D 217/24* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
USPC ........... 514/312, 313, 310; 546/143, 153, 159
See application file for complete search history.

(56) References Cited

U.S. PATENT DOCUMENTS

| | | | |
|---|---|---|---|
| 4,146,637 | A | 3/1979 | Metz et al. |
| 4,456,757 | A | 6/1984 | Hidaka et al. |
| 4,709,032 | A | 11/1987 | Hidaka et al. |
| 4,911,928 | A | 3/1990 | Wallach |
| 4,954,512 | A | 9/1990 | Oguro et al. |
| 5,508,288 | A | 4/1996 | Forbes et al. |
| 5,519,036 | A | 5/1996 | Himmelsbach et al. |
| 5,798,380 | A | 8/1998 | Kaufman et al. |
| 5,891,646 | A | 4/1999 | Barak et al. |
| 6,110,693 | A | 8/2000 | Barak et al. |
| 6,110,912 | A | 8/2000 | Kaufman et al. |
| 6,362,177 | B1 | 3/2002 | Shiota et al. |
| 6,586,425 | B2 | 7/2003 | Kaufman et al. |
| 6,699,891 | B1 | 3/2004 | Kawanishi et al. |
| 6,787,534 | B2 | 9/2004 | Haneda et al. |
| 7,268,143 | B2 | 9/2007 | Jagtap et al. |
| 7,329,684 | B2 | 2/2008 | Mjalli et al. |
| 7,345,158 | B2 | 3/2008 | Egashira et al. |

(Continued)

FOREIGN PATENT DOCUMENTS

| | | |
|---|---|---|
| EP | 0232569 | 8/1987 |
| EP | 0389995 | 10/1990 |

(Continued)

OTHER PUBLICATIONS

Banker, G.S. et al., Modern Pharmaceutics, Marcel Dekker, Inc., New York, (1979) Chapters 9 and 10.

Bird, G.J. et al., "N-methyl as a bioisostere for the oxygen link between the aromatic rings of aryloxyphenoxypropionate herbicides," Bioorg. Med. Chem. Lett. (1997) 7:1489-1492.

Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18):4029-37.

(Continued)

*Primary Examiner* — Kristin Vajda
(74) *Attorney, Agent, or Firm* — Michael Best & Friedrich LLP

(57) ABSTRACT

Disclosed are beta and gamma-amino isoquinoline amide compounds and substituted benzamide compounds. In particular, the invention provides compounds that affect the function of kinases in a cell and that are useful as therapeutic agents or with therapeutic agents. The compounds of the invention are useful in the treatment of a variety of diseases and conditions including eye diseases such as glaucoma, cardiovascular diseases, and diseases characterized by abnormal growth, such as cancers. The invention further provides compositions containing the beta or gamma-amino isoquinoline amide compounds or substituted benzamide compounds.

36 Claims, No Drawings

(56) References Cited

U.S. PATENT DOCUMENTS

| | | |
|---|---|---|
| 7,361,678 B2 | 4/2008 | Mjalli et al. |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,357,699 B2 | 1/2013 | deLong et al. |
| 8,394,826 B2 | 3/2013 | deLong et al. |
| 8,450,344 B2 | 5/2013 | deLong et al. |
| 8,455,513 B2 | 6/2013 | deLong et al. |
| 8,455,514 B2 | 6/2013 | deLong et al. |
| 8,455,647 B2 | 6/2013 | deLong et al. |
| 8,716,310 B2 | 5/2014 | deLong et al. |
| 8,759,388 B2 | 6/2014 | deLong et al. |
| 2004/0091946 A1 | 5/2004 | Oakley et al. |
| 2004/0176462 A1 | 9/2004 | Kawanishi et al. |
| 2005/0032125 A1 | 2/2005 | Oakley et al. |
| 2005/0176712 A1 | 8/2005 | Wakabayashi et al. |
| 2005/0282805 A1 | 12/2005 | Hangeland et al. |
| 2006/0270670 A1 | 11/2006 | Chew et al. |
| 2007/0111983 A1 | 5/2007 | Fong |
| 2007/0123561 A1 | 5/2007 | Lee et al. |
| 2007/0129404 A1 | 6/2007 | Hagihara et al. |
| 2007/0135499 A1 | 6/2007 | deLong et al. |
| 2007/0149473 A1 | 6/2007 | Chatterton et al. |
| 2007/0149548 A1 | 6/2007 | Hellberg et al. |
| 2007/0167444 A1 | 7/2007 | Kuramochi et al. |
| 2007/0238741 A1 | 10/2007 | Nagarathnam et al. |
| 2008/0021026 A1 | 1/2008 | Kahraman et al. |
| 2008/0021217 A1 | 1/2008 | Borchardt |
| 2008/0058384 A1 | 3/2008 | Lee et al. |
| 2008/0096238 A1 | 4/2008 | Sharif et al. |
| 2008/0125427 A1 | 5/2008 | Sehon et al. |
| 2008/0139595 A1 | 6/2008 | Schirok et al. |
| 2008/0153799 A1 | 6/2008 | Laurent et al. |
| 2008/0153813 A1 | 6/2008 | Chen et al. |
| 2008/0161297 A1 | 7/2008 | Bosanac et al. |
| 2008/0194584 A1 | 8/2008 | Birault et al. |
| 2008/0275029 A1 | 11/2008 | Berdini et al. |
| 2009/0005321 A1 | 1/2009 | Zimmer et al. |
| 2009/0069371 A1 | 3/2009 | deLong et al. |
| 2010/0093790 A1 | 4/2010 | deLong et al. |
| 2010/0105650 A1 | 4/2010 | Plettenburg et al. |
| 2010/0144713 A1 | 6/2010 | deLong et al. |
| 2012/0135984 A1 | 5/2012 | deLong et al. |
| 2013/0137721 A1 | 5/2013 | deLong et al. |
| 2014/0187617 A1 | 7/2014 | deLong et al. |
| 2014/0357652 A1 | 12/2014 | Bosanac et al. |

FOREIGN PATENT DOCUMENTS

| | | |
|---|---|---|
| EP | 0482939 | 4/1992 |
| EP | 1550660 | 7/2005 |
| JP | 2005227441 | 8/2005 |
| JP | 2007236388 | 9/2007 |
| JP | 2007246466 | 9/2007 |
| WO | WO 93/18028 | 9/1993 |
| WO | WO 00/76970 | 12/2000 |
| WO | WO 01/37826 | 5/2001 |
| WO | WO 01/47891 | 7/2001 |
| WO | WO 01/53268 | 7/2001 |
| WO | WO 01/53274 | 7/2001 |
| WO | WO 01/56607 | 8/2001 |
| WO | WO 02/22576 | 3/2002 |
| WO | WO 02/32864 | 4/2002 |
| WO | WO 02/085857 | 10/2002 |
| WO | WO 02/085859 | 10/2002 |
| WO | WO 03/073999 | 9/2003 |
| WO | WO 03/080578 | 10/2003 |
| WO | WO 2004/029045 | 4/2004 |
| WO | WO 2004/078747 | 9/2004 |
| WO | WO 2005/020921 | 3/2005 |
| WO | WO 2005/035503 | 4/2005 |
| WO | WO 2005/037257 | 4/2005 |
| WO | WO 2006/041119 | 4/2006 |
| WO | WO 2006/051290 | 5/2006 |
| WO | WO 2006/062982 | 6/2006 |
| WO | WO 2006/076706 | 7/2006 |
| WO | WO 2007/008926 | 1/2007 |
| WO | WO 2007/008942 | 1/2007 |
| WO | WO 2007/060028 | 5/2007 |
| WO | WO 2007/065916 | 6/2007 |
| WO | WO 2007/076360 | 7/2007 |
| WO | WO 2007/076367 | 7/2007 |
| WO | WO 2007/100880 | 9/2007 |
| WO | WO 2007/142323 | 12/2007 |
| WO | WO 2008/011557 | 1/2008 |
| WO | WO 2008/011560 | 1/2008 |
| WO | WO 2008/016016 | 2/2008 |
| WO | WO 2008/036459 | 3/2008 |
| WO | WO 2008/036540 | 3/2008 |
| WO | WO 2008/049000 | 4/2008 |
| WO | WO 2008/049919 | 5/2008 |
| WO | WO 2008/054599 | 5/2008 |
| WO | WO 2008/077057 | 6/2008 |
| WO | WO 2008/077550 | 7/2008 |
| WO | WO 2008/077551 | 7/2008 |
| WO | WO 2008/077552 | 7/2008 |
| WO | WO 2008/077553 | 7/2008 |
| WO | WO 2008/077554 | 7/2008 |
| WO | WO 2008/077555 | 7/2008 |
| WO | WO 2008/077556 | 7/2008 |
| WO | WO 2008/079880 | 7/2008 |
| WO | WO 2008/079945 | 7/2008 |
| WO | WO 2008/086269 | 7/2008 |
| WO | WO 2008/124665 | 10/2008 |
| WO | WO 2009/091898 | 7/2009 |
| WO | WO 2010/011853 | 1/2010 |
| WO | WO 2010/126626 | 11/2010 |
| WO | WO 2010/127329 | 11/2010 |
| WO | WO 2010/127330 | 11/2010 |

OTHER PUBLICATIONS

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Calmes et al., Eur. J. Org. Chem. 2000, 2459-2466.

Capdeville, R. et al., "Glivec (STI571, IMATINIB), A Rationally Developed, Targeted Anticancer Drug", Nature Reviews Drug Discovery (2002) 1:493-502.

Chen, P. et al., "Identification of novel and potent isoquinoline aminooxazole-based IMPDH inhibitors," Bioorg. Med. Chem. Lett. (2003) 13(7):1345-1348.

Cheung, S.T. et al. Can. J. Chern. 1977, 55,906-910.

Dancey, J. et al., "Issues and Progress with Protein Kinase Inhibitors for Cancer Treatment", Nature Reviews Drug Discovery (2003) 2:296-313.

Dorwald, F.Z., Side Reactions in Organic Synthesis. A Guide to Successful Synthesis Design, Wiley-VCH, Weinheim (2005) IX of Preface and 1-15.

Dowton et al., "Influence of Liposomal Composition on Topical Delivery of Encapsulated Cyclosporin A", S.T.P. Pharma Sciences, vol. 3, pp. 404-407 (1993).

Foye, Foye's Principles of Medicinal Chemistry, 5th Edition (2002) Lippencott, Williams, Wilkins, p. 59-63.

G.E. Torres, R.R. Gainetdinov and M.G. Caron (2003). "Plasma membrane monoamine transporters: structure, regulation and function". Nat. Rev. Neurosci. 4 (1): 13-25.

Hackam, A.S. et al., "The Wnt Signaling Pathway in Retinal Degenerations", IUBMB Life (2005) 57(6):381-388.

Hazeldine, S.T. et al., "II. Synthesis and biological evaluation of some bioisosteres and cogeners of the antitumour agent, 2 {4[7-chloro-2-quinoxalinyl)oxy]phenoxy}propionic acid (XK469)," J. Med. Chem. (2002) 45:3130-3137.

He R, Kurome T, Giberson KM, Johnson KM, Kozikowski AP (2005). "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chern. 48 (25): 7970-9.

(56) References Cited

OTHER PUBLICATIONS

Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2-Cyclopropanedicarboxylic Acid and TRANS-2-Phenylcyclopropanecarboxylic Acid", Int'l. J. Org. Chem. (1964) 20(5):1695-1699.
Ito, N. et al., "A medium-term rat liver bioassay for rapid in vivo detection of carcinogenic potential of chemicals," Cancer Science, Jan. 2003, vol. 94, No. 1, pp. 3-8.
Karaman, M.W. et al., "A quantitative analysis of kinase inhibitor selectivity," Nature Biotech. (2008) 26(1):127-132.
Liljebris, C. et al., "Derivatives of 17- Phenyl-18,19,20-trinorprostaglandin F2α Isopropyl Ester: Potential Antiglaucoma Agents," J. Med. Chem. (1995) 38(2):289-304.
Loge, C; Siomboing, X et al. J, of Enzy Inhib & Med Chem, 2003,18,127-128.
Matsui, T. et al., "Novel 5-HT3 antagonists. Isoquinolinones and 3-aryl-2-pyridones," J. Med. Chem. (1992) 35:3307-3319.
McCutcheon's, "Emulsifiers & Detergents", North American Edition (1994) vol. 1:236-239.
Nakanishi et al. FEBS Letters 368, (1995) 411-414.
Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.
Parang, K. et al., "Design strategies for protein kinase inhibitors," Curr. Opin. in Drug Disc. & Dev. (2004) 7(5):617-629.
Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.
Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.
Pharmasolve (N-Methyl-2-Pyrrolidone) product spcification, International Specialty Products, 2000, 10 pages.
Shankar, G. et al., "Protein-kinase-specific inhibitors block Langerhans' cell migration by inhibiting interleukin-1α release", Immunology (1999) 96:230-235.
Stirewalt, D.L. et al., "The Role of FLT3 in Haematopoietic Malignancies", Nature Reviews Cancer (2003) 3:650-665.
STN Registry Database entry for CAS RN 309903-43-6, Published in database Dec. 20, 2000.
Tamura, M., et al., "Development of specific Rho-kinase inhibitors and their clinical application," Biochimica et Biophysica Acta, 2005, vol. 1754, pp. 245-252.
Van Muijlwijk-Koezen et al., "A novel class of adenosine A3 receptor-ligands. 2. Structure affinity profile of a series of isoquinoline and quinazoline compounds," J. Med. Chem. (1998) 41:3994-4000.
Vippagunta et al., "Cystalline solids," 2001, Advanced Drug Delivery Reviews, 48, pp. 3 and 18.
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.
Westra, J. et al., "p38 Mitogen-Activated Protein Kinase (MAPK) in Rheumatoid Arthritis", Mini-Reviews in Medicinal Chemistry (2006) 6(8):867-874.
Jacobs, M. et al., "The structure of dimeric ROCK I reveals the mechanism for ligand selectivity," J. Bio. Chem., 2006, pp. 260-268, published on Jan. 6, 2006.
Meanwell, "Synopsis of some recent tactical application of bioisosteres in drug design," J. Med. Chem., 2011, vol. 54, pp. 2529-2591.
United States Office Action for U.S. Appl. No. 11/485,182 dated Apr. 16, 2009 (13 pages).
United States Office Action for U.S. Appl. No. 12/274,887 dated Jun. 16, 2009 (11 pages).
United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 11/621,887 dated May 18, 2010 (8 pages).
United States Patent Office Action for U.S. Appl. No. 11/621,887 dated Oct. 29, 2010 (14 pages).
United States Patent Office Action for U.S. Appl. No. 13/017,708 dated Apr. 3, 2012 (11 pages).
United States Patent Office Notice of Allowance for U.S. Appl. No. 13/017,708 dated Sep. 17, 2012 (8 pages).
United States Patent Office Notice of Allowance for U.S. Appl. No. 13/017,708 dated Oct. 23, 2012 (7 pages).
United States Patent Office Notice of Allowability for U.S. Appl. No. 13/017,708 dated Dec. 12, 2012 (5 pages).
United States Patent Office Notice of Allowance for U.S. Appl. No. 11/621,887 dated Feb. 27, 2013 (8 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Patent Office Action for U.S. Appl. No. 12/701,963 dated May 10, 2011 (3 pages).
United States Patent Office Action for U.S. Appl. No. 13/230,105 dated Mar. 5, 2012 (8 pages).
United States Patent Office Final Rejection for U.S. Appl. No. 13/230,105 dated Jul. 9, 2012 (11 pages).
United States Patent Office Notice of Allowance for U.S. Appl. No. 13/230,105 dated Mar. 19, 2013 (5 pages).
United States Patent Office Action for U.S. Appl. No. 12/009,326 dated Feb. 3, 2011 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/009,326 dated Feb. 25, 2013 (8 pages).
United States Patent Office Action for U.S. Appl. No. 12/704,822 dated Apr. 30, 2012 (34 pages).
United States Patent Office Final Rejection for U.S. Appl. No. 12/704,822 dated Jan. 16, 2013 (16 pages).
United States Patent Office Action for U.S. Appl. No. 12/704,822 dated Oct. 10, 2013 (11 pages).
United States Patent Office Action for U.S. Appl. No. 12/704,822 dated May 8, 2014 (13 pages).
United States Patent Office Advisory Action for U.S. Appl. No. 11/856,740 dated Feb. 10, 2011 (3 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Patent Office Action for U.S. Appl. No. 12/180,259 dated Jul. 5, 2011 (11 pages).
United States Patent Office Notice of Allowance for U.S. Appl. No. 12/180,259 dated Dec. 19, 2011 (6 pages).
United States Patent Office Notice of Allowance for U.S. Appl. No. 13/442,263 dated Dec. 19, 2012 (13 pages).
United States Patent Office Notice of Allowance for U.S. Appl. No. 13/442,263 dated Feb. 25, 2013 (8 pages).

(56) References Cited

OTHER PUBLICATIONS

United States Patent Office Notice of Allowance for U.S. Appl. No. 13/442,263 dated Jun. 12, 2013 (8 pages).
United States Patent Office Final Rejection for U.S. Appl. No. 13/442,263 dated Dec. 6, 2013 (8 pages).
United States Patent Office Notice of Allowance for U.S. Appl. No. 13/442,263 dated Apr. 15, 2014 (8 pages).
United States Patent Office Action for U.S. Appl. No. 13/318,457 dated Jun. 6, 2013 (12 pages).
United States Patent Office Final Rejection for U.S. Appl. No. 13/318,457 dated Nov. 27, 2013 (13 pages).
United States Patent Office Action for U.S. Appl. No. 12/694,965 dated May 17, 2012 (13 pages).
United States Patent Office Notice of Allowance for U.S. Appl. No. 12/694,965 dated Nov. 2, 2012 (8 pages).
United States Patent Office Notice of Allowance for U.S. Appl. No. 12/694,965 dated Nov. 19, 2012 (4 pages).
United States Patent Office Notice of Allowance for U.S. Appl. No. 13/768,594 dated Oct. 29, 2013 (7 pages).
United States Patent Office Action for U.S. Appl. No. 13/768,594 dated Jul. 10, 2013 (14 pages).
United States Patent Office Action for U.S. Appl. No. 11/856,740 dated Aug. 16, 2013 (14 pages).
United States Patent Office Notice of Allowance for U.S. Appl. No. 11/856,740 dated Apr. 1, 2014 (8 pages).
Partial International Search for Application No. PCT/US2009/031117 dated Apr. 16, 2009 (4 pages).
International Search Report and Written Opinion for Application No. PCT/US2006/026976 dated Feb. 15, 2007 (14 pages).
International Search Report for Application No. PCT/US2006/026947 dated Nov. 17, 2006 (4 pages).
International Preliminary Examination Report for Application No. PCT/US2006/026947 dated Jan. 24, 2008 (10 pages).
International Search Report for Application No. PCT/US08/50374 dated Oct. 28, 2008 (7 pages).
International Preliminary Report on Patentability for Application No. PCT/US08/50374 dated Jul. 14, 2009 (12 pages).
International Search Report and Written Opinion for Application No. PCT/US2009/031117 dated Sep. 24, 2009 (13 pages).
Invitation to Pay Additional Fees and Partial International Search Report for International Application No. PCT/US2009/051569 dated Oct. 15, 2009 (4 pages).
International Search Report and Written Opinion for Application No. PCT/US2009/051569 dated May 20, 2010 (11 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).
International Search Report and Written Opinion for Application No. PCT/US2010/022246 dated Nov. 10, 2010 (7 pages).
International Search Report and Written Opinion for Application No. PCT/US2007/078343 dated Apr. 3, 2008 (12 pages).
European Patent Office Action for Application No. 09702189.3 dated Feb. 1, 2011 (5 pages).
European Patent Office Action for Application No. 09702189.3 dated Dec. 28, 2011 (5 pages).
European Patent Office Action for Application No. 09790775.2 dated Oct. 24, 2011 (5 pages).
Examination Report from the Australian Patent Office for Application No. 2009273932 dated Mar. 13, 2013 (3 pages).
Japanese Patent Office Action for Application No. 2011-520203 dated Jan. 24, 2014 (8 pages, English translation included).
Second Office Action from the Austrialian Intellectual Property Office for Application No. 2009273932 dated Apr. 16, 2012 (2 pages).
Australian Patent Examination Report No. 2 for Application No. 2009273932 dated Jun. 6, 2014 (2 pages).
United States Patent Office Notice of Allowance for U.S. Appl. No. 12/704,822 dated Sep. 9, 2014 (11 pages).
United States Patent Office Notice of Allowance for U.S. Appl. No. 13/723,811 dated Aug. 19, 2014 (11 pages).
United States Patent Office Action for U.S. Appl. No. 14/138,592 dated Jul. 28, 2014 (17 pages).
United States Patent Office Action for U.S. Appl. No. 14/138,592 dated Dec. 9, 2014 (13 pages).
United States Patent Office Action for U.S. Appl. No. 14/461,597 dated Jan. 30, 2015 (19 pages).
Japanese Patent Office Action for Application No. 2014-131231 dated Jan. 14, 2015 (8 pages, English translation attached).
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Olson, "Application for ROCK kinase inhibition," Current Opinion in Cell Biology, 2008, vol. 20, pp. 242-248.
Yamashita et al., "The therapeutic effects of Rho-Rock inhibitors on CNS disorder," Therapeutics and Clinical Risk Management, 2008, vol. 4, pp. 605-615.
Rashid et al., "Development of Rho-kinase inhibitors for cardiovascular medicine," Trends in Pharmacological Science, 2007, vol. 28, pp. 296-302.
Pardridge, "The Blood-Brain Barrier: Bottleneck in Brain Drug development," J. Am. Soc. Exper. NeuroTherapeutics, 2005, vol. 2, p. 3-14.

BETA- AND GAMMA-AMINO-ISOQUINOLINE AMIDE COMPOUNDS AND SUBSTITUTED BENZAMIDE COMPOUNDS

CROSS-REFERENCE TO RELATED APPLICATIONS

This application is a continuation of and claims priority to U.S. patent application Ser. No. 13/442,263, filed Apr. 9, 2012, which is a divisional of and claims priority to U.S. patent application Ser. No. 12/180,259, filed Jul. 25, 2008, which are incorporated herein by reference in their entireties.

FIELD OF THE INVENTION

The present invention relates to beta and gamma-amino isoquinoline amide compounds and substituted benzamide compounds that affect the function of kinases in a cell and that are useful as therapeutic agents or with therapeutic agents. In particular, these compounds are useful in the treatment of eye diseases such as glaucoma, for the treatment of cardiovascular diseases, and for diseases characterized by abnormal growth, such as cancers.

BACKGROUND

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors. The biological effects of activating these receptors is not direct but is mediated by a host of intracellular proteins. The importance of these secondary proteins has only recently been recognized and investigated as intervention points in disease states. One of the most important classes of these downstream effectors is the "kinase" class.

The various kinases thus play important roles in the regulation of various physiological functions. For example, kinases have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis. The importance of p38 MAPK inhibitors in particular as new drugs for rheumatoid arthritis is reflected by the large number of compounds that has been developed over the last years (J. Westra and P. C. Limburg Mini-Reviews in Medicinal Chemistry Volume 6, Number 8, August 2006). Other conditions include chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (e.g., cardiac malformations), neurodegenerative diseases such as Parkinson's Disease and Alzheimer's Disease, multiple sclerosis, Epstein-Barr infection and cancer (*Nature Reviews Drug Discovery* 2002, 1: 493-502). In other disease states, the role of kinases is only now becoming clear. The retina is a complex tissue composed of multiple interconnected cell layers, highly specialized for transforming light and color into electrical signals that are perceived by the brain. Damage or death of the primary light-sensing cells, the photoreceptors, results in devastating effects on vision. Despite the identification of numerous mutations that cause inherited retinal degenerations, the cellular and molecular mechanisms leading from the primary mutations to photoreceptor apoptosis are not well understood, but may involve the wnt pathway (A S Hackam "The Wnt Signaling Pathway in Retinal Degeneration" *IUBMB Life* Volume 57, Number 6/June 2005).

The success of the tyrosine-kinase inhibitor STI571 (Gleevec) in the treatment of chronic myelogenous leukaemia (*Nature Reviews Drug Discovery* 2003, 2: 296-313) has spurred considerable efforts to develop other kinase inhibitors for the treatment of a wide range of other cancers (*Nature Reviews Cancer* 2003, 3: 650-665). The balance between the initiation and the inactivation of intracellular signals determines the intensity and duration of the response of the receptors to stimuli such as agonists. When desensitization occurs, the mediation or regulation of the physiological function mediated or regulated by the G proteins to which the receptors are coupled is reduced or prevented. For example, when agonists are administered to treat a disease or condition by activation of certain receptors, the receptors relatively quickly become desensitized from the action of the GRKs such that agonist administration may no longer result in therapeutic activation of the appropriate receptors. At that point, administration of the agonist no longer enables sufficient or effective control of or influence on the disease or condition intended to be treated.

In view of the role that kinases have in many disease states, there is an urgent and continuing need for small molecule ligands which inhibit or modulate the activity of kinases. Without wishing to be bound by theory, it is thought that modulation of the activity of kinases by the compounds of the present invention is responsible for their beneficial effects.

SUMMARY

In a first aspect of the invention, a compound is provided according to Formula I:

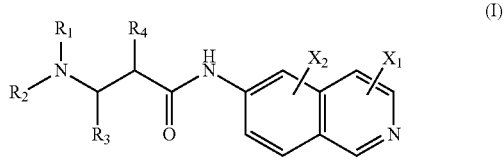

(I)

wherein $R_1$ and $R_2$ are, independently, hydrogen, $C_1$-$C_4$ alkyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; or $R_1$ and $R_2$ combine to form a heterocycloalkyl ring of at least 5 and at most 8 member atoms, or $R_1$ and $R_3$ combine to form a heterocycloalkyl ring of at least 5 and at most 8 member atoms; and wherein one of $R_3$ and $R_4$ is an aryl group, a heteroaryl group, a cycloalkyl group, a heterocycloalkyl group, $C_1$-$C_8$ alkyl, $C_2$-$C_8$ alkenyl, $C_2$-$C_8$ alkynyl, and the other of $R_3$ and $R_4$ is hydrogen or $C_1$-$C_4$ alkyl, the stereocenters being either 'R' or 'S' in configuration independently; and wherein $X_1$ and $X_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In a second aspect of the invention, a compound is provided according to Formula II:

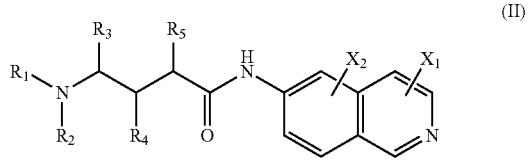

II wherein $R_1$ and $R_2$ are, independently, hydrogen, $C_1$-$C_4$ alkyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; or $R_1$ and $R_2$ combine to form a heterocycloalkyl ring of at least 5 and at most 8 member atoms; or $R_1$ and $R_3$ combine to form a heterocycloalkyl ring of at least 5 and at least 8 member atoms; and wherein one of $R_3$, $R_4$ and $R_5$ is an aryl group, a heteroaryl group, a cycloalkyl group, a heterocycloalkyl group, $C_1$-$C_8$ alkyl, $C_2$-$C_8$ alkenyl, $C_2$-$C_8$ alkynyl, and the other two of $R_3$, $R_4$ and $R_5$ are, independently, hydrogen or $C_1$-$C_4$ alkyl, the stereocenters being either 'R' or 'S' in configuration independently; and wherein $X_1$ and $X_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In a third aspect of the invention, a compound is provided according to Formula III:

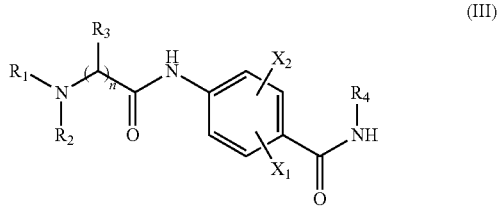

III wherein $R_1$, $R_2$ and $R_4$ are, independently, hydrogen, $C_1$-$C_4$ alkyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; or $R_1$ and $R_2$ combine to form an alkyl or heteroalkyl ring of at least 5 and at most 8 member atoms, or $R_1$ and $R_3$ combine to form an alkyl or heteroalkyl ring of at least 5 and at most 8 member atoms; and wherein one of the $R_3$ groups is an aryl group, a heteroaryl group, a cycloalkyl group, a heterocycloalkyl group, $C_1$-$C_8$ alkyl, $C_2$-$C_8$ alkenyl, $C_2$-$C_8$ alkynyl, and the other $R_3$ groups are, independently, hydrogen or $C_1$-$C_4$ alkyl, the stereocenters being either 'R' or 'S' in configuration independently; and wherein n is 1 to 4; and wherein, $X_1$ and $X_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In another aspect of the invention, a composition is provided, comprising a compound according to Formula I, II, or III as described above, and a carrier.

In yet a further aspect of the invention, a method of treating a disease is provided, comprising administering to a subject in need of treatment effective amount of a compound according to Formula I, II, or III as described above, wherein the disease is selected from the group consisting of eye disease, bone disorder, obesity, heart disease, hepatic disease, renal disease, pancreatitis, cancer, myocardial infarct, gastric disturbance, hypertension, fertility control, disorders of hair growth, nasal congestion, neurogenic bladder disorder, gastrointestinal disorder, and dermatological disorder.

In another aspect of the invention, a method of modulating kinase activity is provided, comprising contacting a cell with a compound according to the Formula I, II or III in an amount effective to modulate kinase activity

DETAILED DESCRIPTION

Publications and patents are referred to throughout this disclosure. All U.S. patents cited herein are hereby incorporated by reference. All percentages, ratios, and proportions used herein are percent by weight unless otherwise specified.

Beta- and gamma-amino isoquinolines and benzamides are provided.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. More than one substituent may be present. Substituents may also be themselves substituted. When substituted, the substituent group is preferably but not limited to $C_1$-$C_4$ alkyl, aryl, heteroaryl, amino, imino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. More than one substituent may be present. When substituted, the substituent group is preferably alkyl, halogen or alkoxy. Substitutients may also be themselves substituted. Substituents can be placed on the alkene itself and also on the adjacent member atoms or the alkynyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. More than one substituent may be present. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl; alkenyl; alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl.

"Amino" refers to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidinyl is specifically contemplated under the term 'amino".

"Aryl" refers to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to heteroaryl; acyl, carboxyl, carbonylamino, nitro, amino, cyano, halogen, or hydroxyl.

"Carboxyl" refers to the group —C(=O)O—$C_1$-$C_4$ alkyl.

"Carbonyl" refers to the group —C(O)R wherein each R is, independently, hydrogen, alkyl, aryl, cycloalkyl; heterocycloalkyl; heteroaryl, $C_1$-$C_4$ alkyl aryl or $C_1$-$C_4$ alkyl heteroaryl.

"Carbonylamino" refers to the group —C(O)NR'R' wherein each R' is, independently, hydrogen, alkyl, aryl, cycloalkyl; heterocycloalkyl; heteroaryl, $C_1$-$C_4$ alkyl aryl or $C_1$-$C_4$ alkyl heteroaryl. The two R' groups may themselves be linked to form a ring.

"$C_1$-$C_1$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. More than one substituent may be present. Substituents may also be themselves substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl; thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. More than one substituent may be present. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxy is hydroxyl.

"Linker" means a linear chain of n member atoms where n is an integer of from 1 to 4.

"Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. More than one substituent may be present. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S— alkyl.

"Sulfonyl" refers to the —S(O)$_2$R' group wherein R' is alkoxy, alkyl, aryl, carbocyclic, heterocarbocyclic; heteroaryl, $C_1$-$C_4$ alkyl aryl or $C_1$-$C_4$ alkyl heteroaryl.

"Sulfonylamino" refers to the —S(O)$_2$NR'R' group wherein each R' is independently alkyl, aryl, heteroaryl, $C_1$-$C_4$ alkyl aryl or $C_1$-$C_4$ alkyl heteroaryl.

"Pharmaceutically acceptable carrier" means a carrier that is useful for the preparation of a pharmaceutical composition that is: generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Therapeutically effective amount" as used herein refers to a dosage of the compounds or compositions effective for influencing, reducing or inhibiting the activity of or preventing activation of a kinase. This term as used herein may also refer to an amount effective at bringing about a desired in vivo effect in an animal, preferably, a human, such as reduction in intraocular pressure.

"Administering" as used herein refers to administration of the compounds as needed to achieve the desired effect.

"Eye disease" as used herein includes, but is not limited to, glaucoma, allergy, cancers of the eye, neurodegenerative diseases of the eye, and dry eye.

The term "disease or condition associated with kinase activity" is used to mean a disease or condition treatable, in whole or in part, by inhibition of one or more kinases.

The term "controlling the disease or condition" is used to mean changing the activity of one or more kinases to affect the disease or condition.

The term "contacting a cell" is used to mean contacting a cell in vitro or in vivo (i.e. in a subject, such as a mammal, including humans, rabbits, cats and dogs).

The beta-amino isoquinoline amide compounds may be represented by Formula I:

I

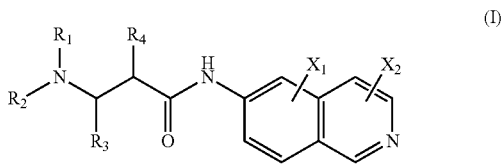

(I)

wherein $R_1$ and $R_2$ are, independently, hydrogen, $C_1$-$C_4$ alkyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; or $R_1$ and $R_2$ combine to form a heterocycloalkyl ring of at least 5 and at most 8 member atoms, or $R_1$ and $R_3$ combine to form a heterocycloalkyl ring of at least 5 and at most 8 member atoms; and wherein one of $R_3$ and $R_4$ is an aryl group, a heteroaryl group, a cycloalkyl group, a heterocycloalkyl group, $C_1$-$C_8$ alkyl, $C_2$-$C_8$ alkenyl, $C_2$-$C_8$ alkynyl, and the other of $R_3$ and $R_4$ is hydrogen or $C_1$-$C_4$ alkyl, the stereocenters being either 'R' or 'S' in configuration independently, wherein $X_1$ and $X_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In a preferred embodiment of Formula I, $R_1$ and $R_2$ are methyl groups or hydrogens, $R_4$ is an aryl or heteroaryl group and $R_3$ and $X_2$ are hydrogen. In another preferred embodiment of Formula I, $R_1$ is a cycloalkyl group, and $R_2$ is hydrogen and $R_3$ are methyl and $X_1$ is a hydroxyl group.

The gamma-amino isoquinoline amide compounds may be represented by Formula II:

II

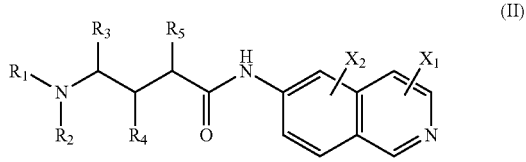

(II)

wherein $R_1$ and $R_2$ are, independently, hydrogen, $C_1$-$C_4$ alkyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; or $R_1$ and $R_2$ combine to form a heterocycloalkyl ring of at least 5 and at most 8 member atoms; and wherein one of $R_3$, $R_4$ and $R_5$ is an aryl group, a heteroaryl group, a cycloalkyl group, a heterocycloalkyl group, $C_1$-$C_8$ alkyl, $C_2$-$C_8$ alkenyl, $C_2$-$C_8$ alkynyl, and the other two of $R_3$, $R_4$ and $R_5$ are, independently, hydrogen or $C_1$-$C_4$ alkyl, the stereocenters being either 'R' or 'S' in configuration independently; and wherein $X_1$ and $X_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In a preferred embodiment of Formula II, $R_1$ and $R_2$ are methyl groups or hydrogens, $R_4$ is an aryl or heteroaryl group and $R_3$ and $X_2$ are hydrogen. In another preferred embodiment of Formula II, $R_1$ is a cycloalkyl group, and $R_2$ is a hydrogen and $R_3$ are methyl and $X_1$ is a hydroxyl group.

The benzamide compounds may be represented by Formula III:

II

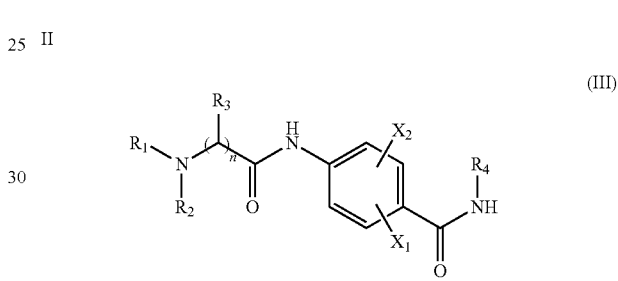

(III)

wherein $R_1$, $R_2$ and $R_4$ are, independently, hydrogen, $C_1$-$C_4$ alkyl, $C_2$-$C_4$ alkenyl, $C_2$-$C_4$ alkynyl, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl; or $R_1$ and $R_2$ combine to form a heterocycloalkyl ring of at least 5 and at most 8 member atoms, or $R_1$ and $R_3$ combine to form a heterocycloalkyl ring of at least 5 and at most 8 member atoms; and wherein one of the $R_3$ groups is an aryl group, a heteroaryl group, a cycloalkyl group, a heterocycloalkyl group, $C_1$-$C_8$ alkyl, $C_2$-$C_8$ alkenyl, $C_2$-$C_8$ alkynyl, and the other $R_3$ groups are, independently, hydrogen or $C_1$-$C_4$ alkyl, the stereocenters being either 'R' or 'S' in configuration independently; and wherein n is 1 to 4; and wherein $X_1$ and $X_2$ are, independently, hydrogen, hydroxyl, halogen, $C_1$-$C_4$ alkyl, $C_2$-$C_4$ alkenyl, $C_2$-$C_4$ alkynyl, amino, nitro, cyano, $C_1$-$C_4$ carbonyl, $C_1$-$C_4$ carbonylamino, $C_1$-$C_4$ alkoxy, $C_1$-$C_4$ sulfonyl, $C_1$-$C_4$ sulfonylamino, $C_1$-$C_4$ thioalkyl or $C_1$-$C_4$ carboxyl.

In a preferred embodiment of Formula III, $R_1$ and $R_2$ are methyl groups or hydrogens, $R_3$ is an aryl or heteroaryl group and $R_4$ and $X_2$ are hydrogen. In another preferred embodiment of Formula III, $R_1$ is a cycloalkyl group, and $R_2$ is a hydrogen and $R_3$ are methyl and $X_1$ is a fluoride or a hydrogen.

In one embodiment of Formula III, n is 1 to 3. Alternatively, n is 2.

The beta or gamma-amino isoquinoline amide or substituted benzamide compounds may be synthesized by the general Schemes 1-7 set forth below:

Scheme 1

Scheme 1. (followed a modified procedure Kaseda et al. *Tet. Lett.* 1989, 30, 4539-4542.)

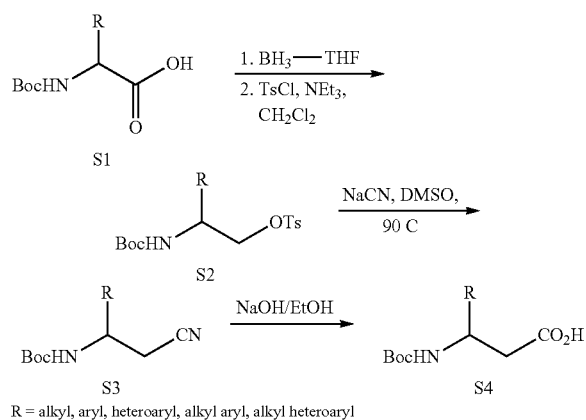

R = alkyl, aryl, heteroaryl, alkyl aryl, alkyl heteroaryl

According to Scheme 1, the selected acid (S1) is reduced with an appropriate agent such as borane then activated as the tosylate to form the desired intermediate (S2). The tosylate (S2) is reacted with the sodium cyanide in DMSO to generate the nitrile (S3) directly which is then hydrolyzed with sodium hydroxide to form the one-carbon longer amino acid (S4). Following this scheme, alpha amino acids are transformed into beta amino acids and beta amino acids are turned into gamma, and gamma to delta in turn.

Scheme 2

Scheme 2.

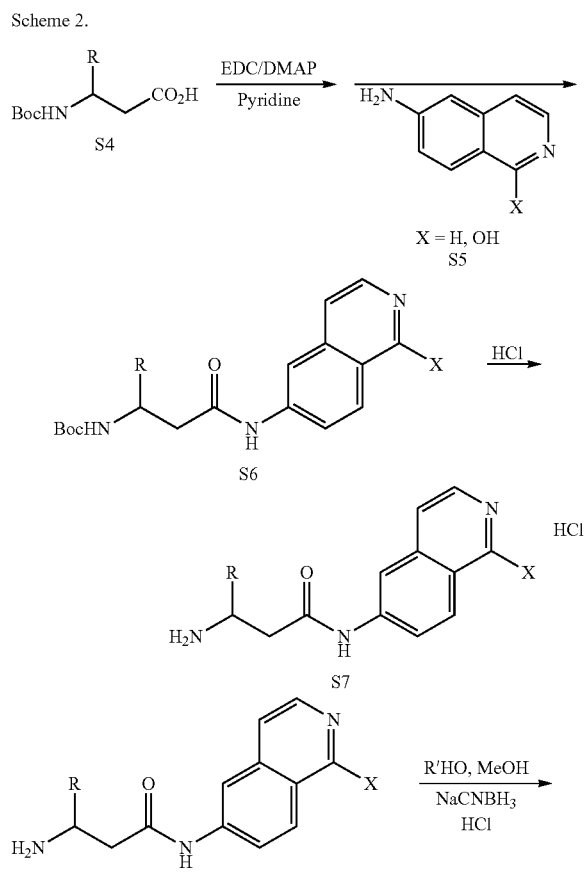

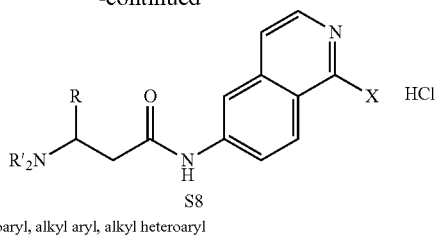

R = alkyl, aryl, heteroaryl, alkyl aryl, alkyl heteroaryl
X = H, OH

According to Scheme 2, the selected acid (S4) is activated with an appropriate agent such as EDC then coupled to a 6-aminoisoquinoline (S5) using standard coupling procedures to form the desired intermediate (S6). The amine (S6) is reacted with the HCl in methylene chloride to generate the amide (S7) directly. When an alkyl group is desired to be added, (S6) is subjected to reductive amination conditions to generate the N,N-disubstituted compounds of type (S8).

Scheme 3

Scheme 2.

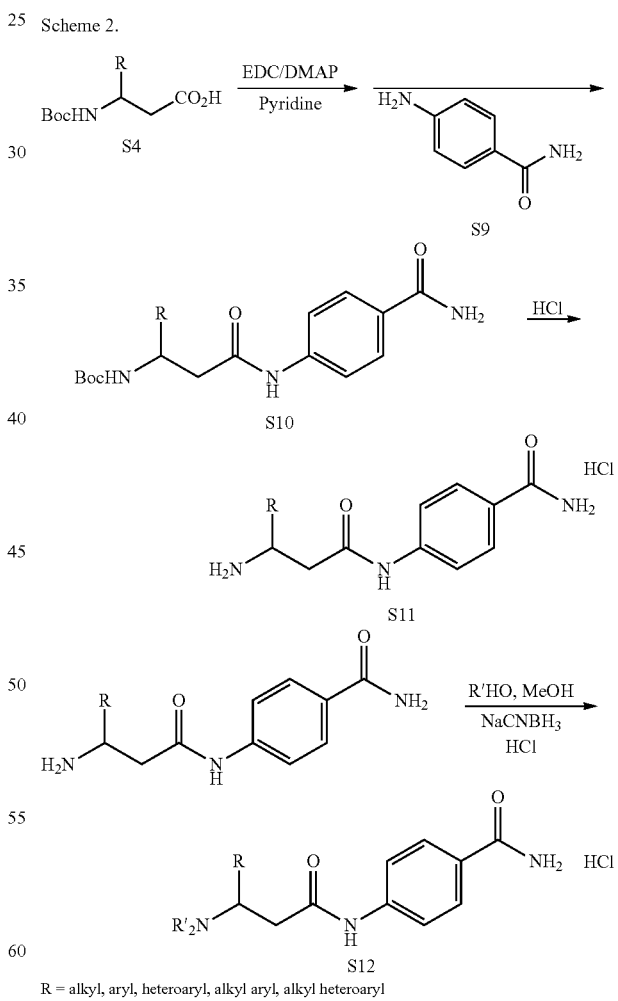

R = alkyl, aryl, heteroaryl, alkyl aryl, alkyl heteroaryl

Benzamidines are synthesized using the procedures outlined in Scheme 2, but substituting the para-amino benzamide of choice for the amino isoquinoline, as shown in Scheme 3.

Scheme 4

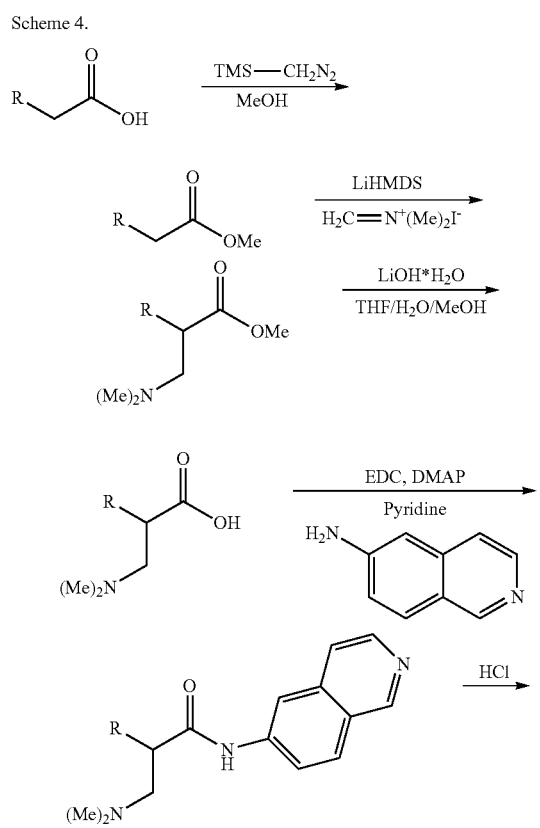

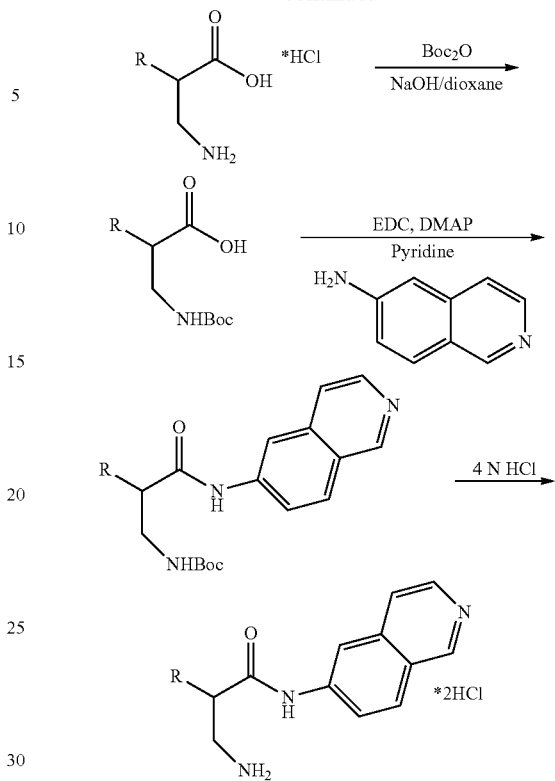

(followed a modified procedure by Calmes et al. Eur. J. Org. Chem. 2000, 2459-2466)

The benzamide compounds may be synthesized by the general Schemes 6-7 set forth below:

Scheme 5

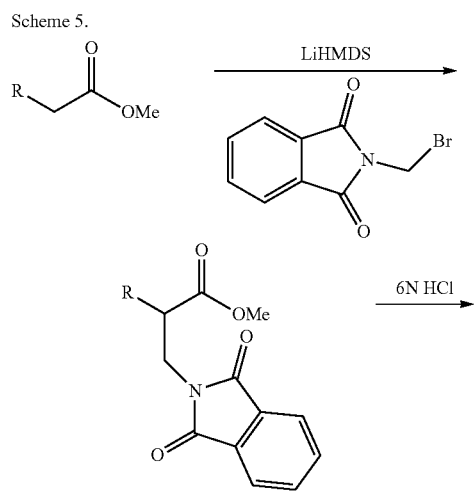

Scheme 6

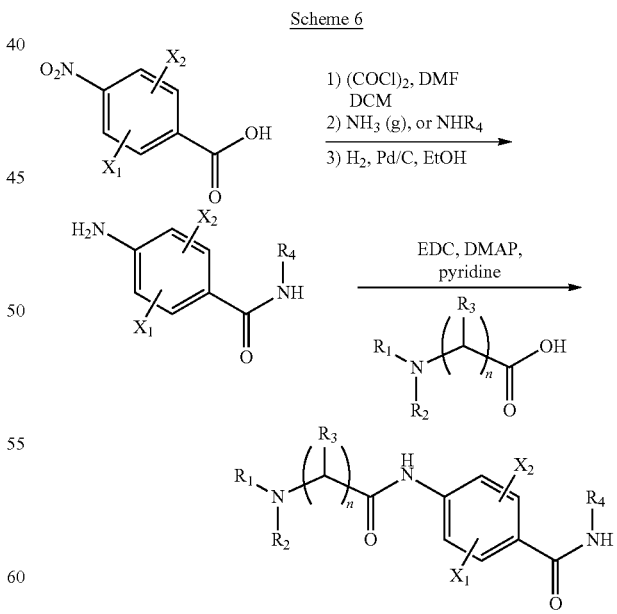

According to Scheme 6, the appropriate acid is converted to its acid chloride with oxalyl chloride then reacted with ammonia gas or another amine to give the amide. The nitro group is reduced to the aniline with hydrogen or another reducing agent. The aniline is coupled with an appropriate acid using standard coupling procedures such as EDC and DMAP in pyridine.

An alternative synthetic route is outlined in Scheme 7:

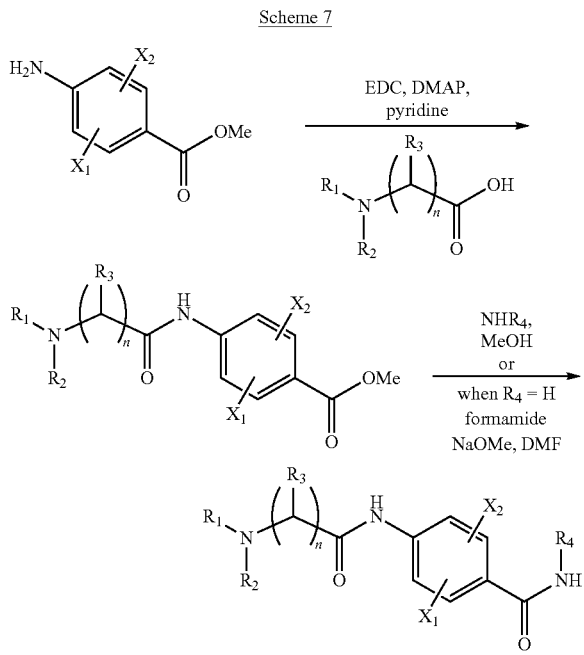

According to Scheme 7, the aniline is coupled with an appropriate acid using standard coupling procedures such as EDC and DMAP in pyridine. The ester is then converted to the corresponding primary amide using formamide and NaOMe in DMF or to a substituted amide by heating with the appropriate amine in a solvent such as MeOH.

The abbreviations used in the synthetic schemes shown have the following meanings: $Boc_2O$ means di-tert-butyl-dicarbonate, DMAP means dimethyl aminopyridine, DMSO means dimethyl sulfoxide, HATU means 2-(7-Aza-1H-benzotriazole-1-yl)-1,1,3,3-tetramethyluronium hexafluorophosphate, LDA means lithium diisopropyl amide, DMF is dimethylformamide, THF is tetrahydrofuran, and EDC means N-(3-dimethylaminopropyl)-N'-ethylcarbodiimide hydrochloride.

The compounds of the above Formulae and compositions including them have kinase inhibitory activity and are thus useful in modulating the action of kinases, and in treatment and/or prevention of diseases or conditions influenced by kinases. The above Formulae and compositions may be used to modulate (e.g., influence or inhibit) the action of kinases either in a cell in vitro or in a cell in a living body in vivo. Specifically, in one embodiment, a method is provided of inhibiting the action of a kinase comprising applying to a medium such as an assay medium or contacting with a cell either in a cell in vitro or in a cell in a living body in vivo an effective inhibitory amount of a compound according to Formulae I or II or III. In a preferred embodiment, the kinase inhibited is a rho kinase.

Compounds according to Formulae I or II or III are used in methods of inhibiting kinases in a cell, a tissue or a subject such as a human comprising contacting the cell with an amount of one or more of the compounds of the present invention effective to inhibit the kinase. In one embodiment, the compounds are administered in a pharmaceutically acceptable composition, such as in or with a pharmaceutically acceptable carrier.

In another embodiment, the compounds of the present invention are used in methods for modulating the action of a kinase in a cell comprising contacting the cell with amount of one or more compounds according to Formulae I or II or III effective to modulate the action of a kinase in a cell. In one embodiment, the compounds of the present invention are administered in a pharmaceutically acceptable composition, such as in or with a pharmaceutically acceptable carrier.

Treatment or prevention of diseases or conditions for which the compounds of the present invention may be useful includes any of the diseases or conditions associated with kinase activity or diseases or conditions affected by kinases. Examples of these types of diseases include retinal degradation, glaucoma, cardiovascular diseases and cancer.

In some embodiments, the compounds of the present invention will be administered in conjunction with one or more additional therapeutic agents. Suitable additional therapeutic agents include, but are not limited to, beta blockers, alpha-agonists, carbonic anhydrase inhibitors, prostaglandin-like compounds, miotic or cholinergic agents, or epinephrine compounds.

Beta Blockers.

These reduce the production of aqueous humor. Examples include levobunolol (Betagan), timolol (Betimol, Timoptic), betaxolol (Betoptic) and metipranolol (OptiPranolol).

Alpha-Agonists.

These reduce the production of aqueous humor and increase drainage. Examples include apraclonidine (Iopidine) and brimonidine (Alphagan).

Carbonic Anhydrase Inhibitors.

These also reduce the production of aqueous humor. Examples include dorzolamide (Trusopt) and brinzolamide (Azopt).

Prostaglandin-Like Compounds.

These eyedrops increase the outflow of aqueous humor. Examples include latanoprost (Xalatan), bimatoprost (Lumigan) and travoprost (Travatan).

Miotic or Cholinergic Agents.

These also increase the outflow of aqueous humor. Examples include pilocarpine (Isopto Carpine, Pilopine) and carbachol (Isopto Carbachol).

Epinephrine Compounds.

These compounds, such as dipivefrin (Propine), also increase the outflow of aqueous humor.

The additional therapeutic agent or agents can be administered simultaneously or sequentially with the compounds of the present invention. Sequential administration includes administration before or after the compounds of the present invention. In some embodiments, the additional therapeutic agent or agents can be administered in the same composition as the compounds of the present invention. In other embodiments, there can be an interval of time between administration of the additional therapeutic agent and the compounds of the present invention.

In some embodiments, the administration of an additional therapeutic agent with a compound of the present invention will enable lower doses of the other therapeutic agents to be administered for a longer period of time.

Compounds of the present invention may be obtained in the form of various salts or solvates. As the salts, physiologically acceptable salts or salts available as raw materials are used.

Compositions may include one or more of the isoforms of the present invention. When racemates exists, each enantiomer or diastereomer may be separately used, or they may be combined in any proportion. Where tautomers exist all possible tautomers are specifically contemplated.

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral or rectal administration. Techniques and formulations may generally be found in "Remington's Pharmaceutical Sciences", (Meade Publishing Co., Easton, Pa.).

The route by which the compounds of the present invention (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds of the present invention and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the compounds of the present invention are topically administered. Topical compositions that can be applied locally to the eye may be in any form known in the art, non-limiting Examples of which include solids, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye. Component B may further comprise one or more optional components.

An effective amount of a compound according to the present invention will vary with the particular condition being treated, the age and physical condition of the patient being treated, the severity of the condition, the duration of treatment, the nature of concurrent therapy, the route of administration, the particular pharmaceutically-acceptable carrier utilized, and like factors within the knowledge and expertise of the attending physician. For example, an effective amount of the compounds of the present invention for systemic administration is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 ng/mL, more preferably from 0.05 to 50 ng/mL and most preferably from 0.1 to 10 ng/mL. While these dosages are based upon a daily administration rate, the compounds of the present invention may also be administered at other intervals, such as twice per day, twice weekly, once weekly, or once a month. One of ordinary skill in the art would be able to calculate suitable effective amounts for other intervals of administration.

The compounds of the present invention are useful in a method of reducing or decreasing intraocular pressure. The compounds of the present invention may be administered to a subject in need of treatment in an amount effective to reduce intraocular pressure. Thus, these compounds are useful in the treatment of glaucoma. The preferred route of administration for treating glaucoma is topically.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.001 to about 0.3%. If the $IC_{50}$ of the medicament is 10 nM, the amount of component A) will be from about 0.01 to about 1%. If the $IC_{50}$ of the medicament is 100 nM, the amount of component A will be from about 0.1 to about 10%. If the $IC_{50}$ of the medicament is 1000 nM, the amount of component A will be 1 to 100%, preferably 5% to 50%. If the amount of component A is outside the ranges specified above (i.e., lower), efficacy of the treatment may be reduced. One skilled in the art understands how to calculate and understand an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, *aloe vera* gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In a particularly preferred embodiment of the invention, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 5.0-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The invention will be further explained by the following illustrative Examples that are to be considered to be non-limiting.

Specific procedures for the preparation of beta and gamma-amino isoquinoline amide compounds and substituted benzamide compounds are described in the following Examples.

All temperatures are in degrees Centigrade. Reagents and starting materials were purchased from commercial sources or prepared following published literature procedures.

Unless otherwise noted, HPLC purification, when appropriate, was performed by redissolving the compound in a small volume of DMSO and filtering through a 0.45 micron (nylon disc) syringe filter. The solution was then purified using, for example, a 50 mm Varian Dynamax HPLC 21.4 mm Microsorb Guard-8 $C_8$ column. A typical initial eluting mixture of 40-80% MeOH:$H_2O$ was selected as appropriate for the target compound. This initial gradient was maintained for 0.5 minutes then increased to 100% MeOH:0% $H_2O$ over 5 minutes. 100% MeOH was maintained for 2 more minutes before re-equilibration back to the initial starting gradient. A typical total run time was 8 minutes. The resulting fractions were analyzed, combined as appropriate, and then evaporated to provide purified material.

Proton magnetic resonance ($^1H$ NMR) spectra were recorded on either a Varian NOVA 600 MHz ($^1H$) NMR spectrometer, Varian INOVA 500 MHz ($^1H$) NMR spectrometer, Varian Mercury 300 MHz ($^1H$) NMR spectrometer, or a Varian Mercury 200 MHz ($^1H$) NMR spectrometer. All spectra were determined in the solvents indicated. Although chemical shifts are reported in ppm downfield of tetramethylsilane, they are referenced to the residual proton peak of the respective solvent peak for $^1H$ NMR. Interproton coupling constants are reported in Hertz (Hz).

Analytical LCMS spectra were obtained using a Waters ZQ MS ESI instrument with an Alliance 2695 HPLC and a 2487 dual wavelength UV detector. Spectra were analyzed at 254 and 230 nm. Samples were passed through a Waters Symmetry C18 4.6×75 mm 3.5µ column with or without a guard column (3.9×20 mm 5µ). Gradients were run with mobile phase A: 0.1% formic acid in $H_2O$ and mobile phase B: ACN with a flow rate of 0.8 mL/min. Two gradients will illustrate:

| Gradient A | | |
|---|---|---|
| Time | A% | B% |
| 0.00 | 80.0 | 20.0 |
| 1.00 | 80.0 | 20.0 |
| 6.00 | 25.0 | 75.0 |
| 7.00 | 5.0 | 95.0 |
| 8.00 | 5.0 | 95.0 |
| 9.00 | 80.0 | 20.0 |
| 12.00 | 80.0 | 20.0 |

| Gradient B | | |
|---|---|---|
| Time | A% | B% |
| 0.00 | 80.0 | 20.0 |
| 1.00 | 80.0 | 20.0 |
| 6.00 | 25.0 | 75.0 |
| 7.00 | 5.0 | 95.0 |
| 8.00 | 5.0 | 95.0 |
| 9.00 | 80.0 | 20.0 |
| 12.00 | 80.0 | 20.0 |

The settings for the MS probe were a cone voltage at 38 mV and a desolvation temperature at 250° C. Any variations in these methods are noted below.

The following preparations illustrate procedures for the preparation of intermediates and methods for the preparation of a beta or gamma-amino isoquinoline amide derivative or substituted benzamide derivatives.

EXAMPLES

Example 1

Preparation of tert-butyl 2-hydroxy-1-(thiophen-3-yl)ethylcarbamate (E1)

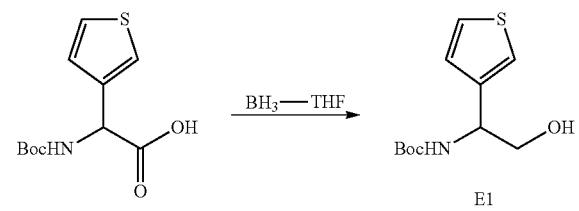

To (±)-2-(tert-butoxycarbonylamino)-2-(thiophen-3-yl) acetic acid in THF at 0° C. was added $BH_3$-THF dropwise. The solution was allowed to warm to room temperature and stirred for an additional 2 hours. The solution was cooled to 0° C., quenched with AcOH (10%)/MeOH and evaporated. Column chromatography ($SiO_2$, EtOAc) gave pure tert-butyl 2-hydroxy-1-(thiophen-3-yl)ethylcarbamate (E1).

Example 2

Preparation of 2-(tert-butoxycarbonylamino)-2-(thiophen-3-yl)ethyl 4-methylbenzenesulfonate (E2)

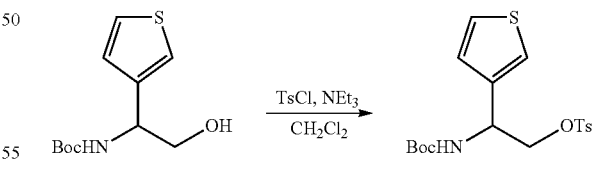

To tert-butyl 2-hydroxy-1-(thiophen-3-yl)ethylcarbamate (E1) in $CH_2Cl_2$ was added $NEt_3$, DMAP, and TsCl. The solution was stirred at room temperature for 3 hours and then poured into $NH_4Cl$ (sat) and extracted with EtOAc, dried ($Na_2SO_4$), filtered, and evaporated. Column chromatography ($SiO_2$, 30% EtOAc/Hexanes) gave pure 2-(tert-butoxycarbonylamino)-2-(thiophen-3-yl)ethyl 4-methylbenzenesulfonate (E2).

Example 3

Preparation of tert-butyl 2-cyano-1-(thiophen-3-yl)ethylcarbamate (E3)

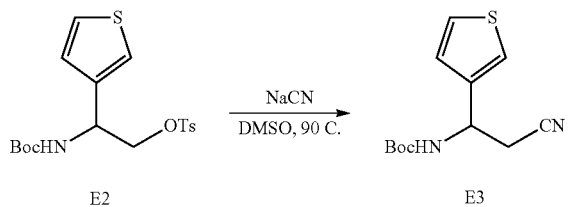 [SMILES: Cc1ccc(S(=O)(=O)OCC(NC(=O)OC(C)(C)C)c2ccsc2)cc1 ; "NaCN" ; "DMSO, 90 C." ; CC(C)(C)OC(=O)NC(CC#N)c1ccsc1]

To 2-(tert-butoxycarbonylamino)-2-(thiophen-3-yl)ethyl 4-methylbenzenesulfonate (E2) in DMSO was added NaCN, and the solution was heated to 90° C. for 2 hours. The reaction was cooled, poured into NaCl (sat), and extracted with EtOAc. The organics were dried ($Na_2SO_4$), filtered, and evaporated. Column chromatography ($SiO_2$, 25% EtOAc/Hexanes) gave pure tert-butyl 2-cyano-1-(thiophen-3-yl)ethylcarbamate (E3).

Example 4

Preparation of 3-(tert-butoxycarbonylamino)-3-(thiophen-3-yl)propanoic acid (E4)

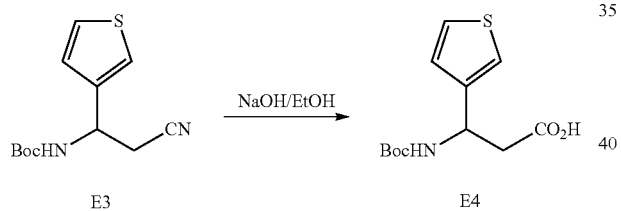

To tert-butyl 2-cyano-1-(thiophen-3-yl)ethylcarbamate (E3) in EtOH was added NaOH (2M), and the solution was heated to 90° C. for 4 hours. The reaction was cooled, acidified with HCl, and extracted with EtOAc. The organics were dried ($Na_2SO_4$) and evaporated to give pure 3-(tert-butyoxycarbonylamino)-3-(thiophen-3-yl)propanoic acid (E4).

Example 5

Preparation of tert-butyl 3-(isoquinolin-6-ylamino)-3-oxo-1-(thiophen-3-yl)propylcarbamate (E5)

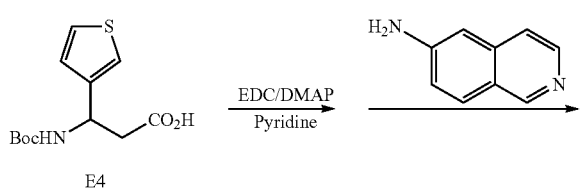

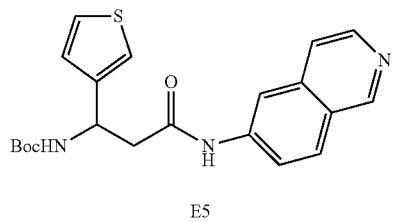

To 3-(tert-butyoxcarbonylamino)-3-(thiophen-3-yl)propanoic acid (E4) in pyridine was added EDC, DMAP, and 6-aminoisoquinoline. The solution was stirred for 10 hours at room temperature. The mixture was poured into $NaHCO_3$ (sat) and extracted with EtOAc, dried ($Na_2SO_4$), filtered, and evaporated. Column chromatography ($SiO_2$, 5% MeOH/$CH_2Cl_2$) gave pure tert-butyl 3-(isoquinolin-6-ylamino)-3-oxo-1-(thiophen-3-yl)propylcarbamate (E5).

Example 6

Preparation of 3-amino-N-(isoquinolin-6-yl)-3-(thiophen-3-yl)propanamide dihydrochloride (E6)

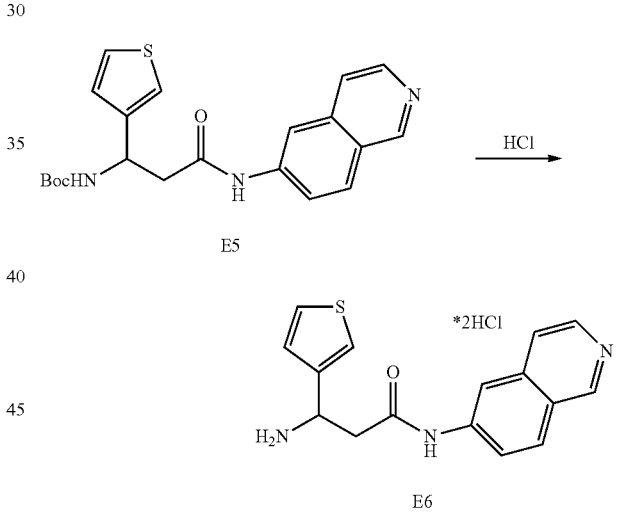

To tert-butyl 3-(isoquinolin-6-ylamino)-3-oxo-1-(thiophen-3-yl)propylcarbamate (E5) in $CH_2Cl_2$ was added HCl (4N in dioxane), and the solution was stirred for 8 hours. The solvents were evaporated to give 3-amino-N-(isoquinolin-6-yl)-3-(thiophen-3-yl)propanamide dihydrochloride (E6).

Examples 7-40

Using commercially available compounds and largely the procedures set forth in Examples 1-6 and substituting the appropriate starting materials, the compounds 7-11, 13-16, 18-21, and 25 were made, and compounds 12, 17, 22-24, and 26-40 can be made.

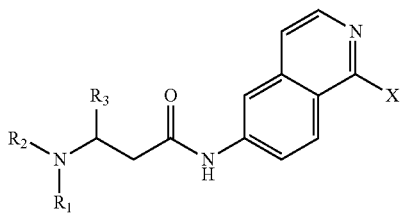

| Example | X  | R₃                  | R₂ | R₁ |
|---------|----|---------------------|----|----|
| 7       | H  | (S)—C₆H₅            | H  | H  |
| 8       | H  | (R)—C₆H₅            | H  | H  |
| 9       | OH | (S)—C₆H₅            | H  | H  |
| 10      | OH | (R)—C₆H₅            | H  | H  |
| 11      | OH | (S)—C₆H₅            | Me | Me |
| 12      | H  | (S)—C₆H₅            | Me | H  |
| 13      | H  | (±)-o-chloro-C₆H₄   | H  | H  |
| 14      | OH | (±)-o-chloro-C₆H₄   | H  | H  |
| 15      | H  | (±)-p-fluoro-C₆H₄   | H  | H  |
| 16      | OH | (±)-p-fluoro-C₆H₄   | H  | H  |
| 17      | H  | (±)-p-fluoro-C₆H₄   | Me | H  |
| 18      | H  | (S)-3-thienyl       | H  | H  |
| 19      | OH | (S)-3-thienyl       | H  | H  |
| 20      | H  | (S)-3-thienyl       | Me | Me |
| 21      | OH | (S)-3-thienyl       | Me | Me |
| 22      | H  | (R)-3-thienyl       | Me | Me |
| 23      | OH | (R)-3-thienyl       | Me | Me |
| 24      | OH | (S)-3-thienyl       | Me | H  |
| 25      | H  | (S)-2-thienyl       | Me | Me |
| 26      | H  | (R)-2-thienyl       | Me | Me |
| 27      | H  | 3-furyl             | H  | H  |
| 28      | OH | 2-furyl             | Me | Me |
| 29      | OH | 3,5-difluoroC₆H₃    | Me | H  |
| 30      | H  | m-CH₃               | H  | H  |
| 31      | H  | 2-pyridyl           | H  | H  |
| 32      | OH | 4-pyridyl           | Me | Me |
| 33      | H  | Benzyl              | H  | H  |
| 34      | H  | Cyclohexyl          | Me | Me |
| 35      | H  | Cyclopropyl         | H  | H  |
| 36      | OH | Methyl cyclohexyl   | Me | H  |
| 37      | H  | 4-fluorobenzyl      | H  | H  |
| 38      | H  | 2-thiazole          | Me | Me |
| 39      | OH | 2-oxazole           | H  | Me |
| 40      | H  | 3-piperdyl          | Me | Me |

Example 41

Preparation of methyl 2-(thiophen-3-yl)acetate (E41)

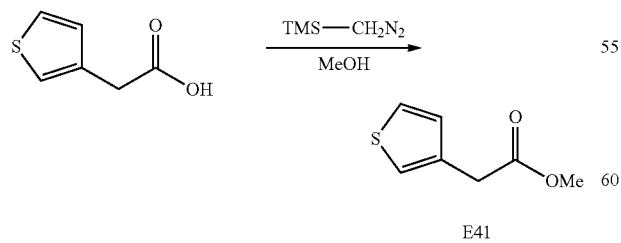

To 2-(thiophen-3-yl)acetic acid in MeOH at 0° C. was added TMS-CH₂N₂. The solution was stirred for 3 hours then quenched with a few drops of AcOH. The solvents were evaporated. Column chromatography (SiO₂, 3-15% EtOAc/Hex) gave pure methyl 2-(thiophen-3-yl)acetate (E41).

Example 42

Preparation of methyl 3-(dimethylamino)-2-(thiophen-3-yl)propanoate (E42)

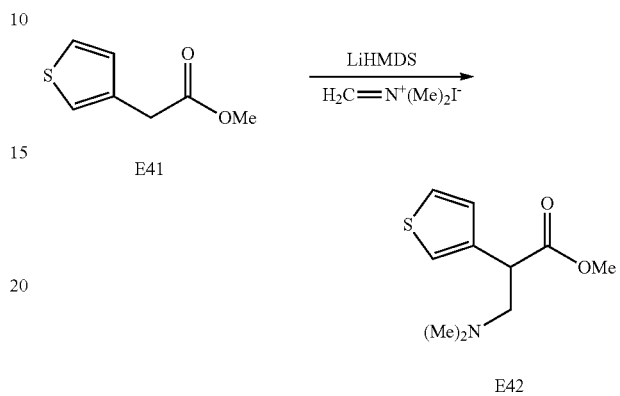

To methyl 2-(thiophen-3-yl)acetate (E41) in THF cooled to −78° C. was added LiHMDS, and the solution stirred at −78° C. for 30 min. Then N,N-Dimethylmethyleneiminium iodide was added directly and the solution was allowed to warm to 0° C. The mixture was poured into NaHCO₃ (sat), extracted with EtOAc, dried (Na₂SO₄), filtered, and evaporated. Column chromatography (SiO₂, 5% MeOH/CH₂Cl2) gave pure methyl 3-(dimethylamino)-2-(thiophen-3-yl)propanoate (E42).

Example 43

Preparation of 3-(dimethylamino)-2-(thiophen-3-yl) propanoic acid (E43)

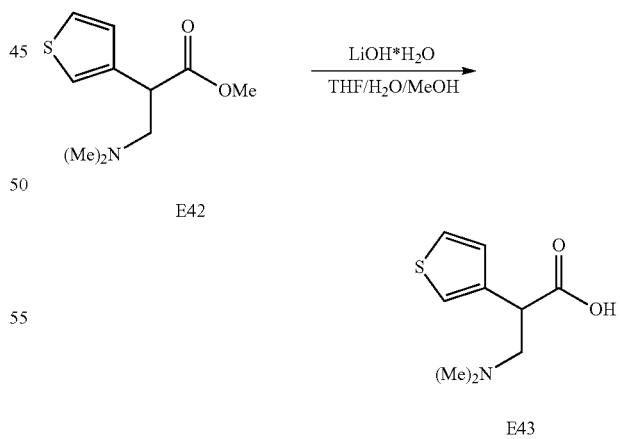

To methyl 3-(dimethylamino)-2-(thiophen-3-yl)propanoate (E42) in THF/H₂O/MeOH was added LiOH*H₂O, and the solution was stirred for 12 hours. AcOH was added and the solvents were evaporated. Column chromatography (SiO₂, 10-15% 2M NH₃-MeOH/EtOH) gave pure 3-(dimethylamino)-2-(thiophen-3-yl)propanoic acid (E43).

Example 44

Preparation of 3-(dimethylamino)-N-(isoquinolin-6-yl)-2-(thiophen-3-yl)propanamide dihydrochloride (E44)

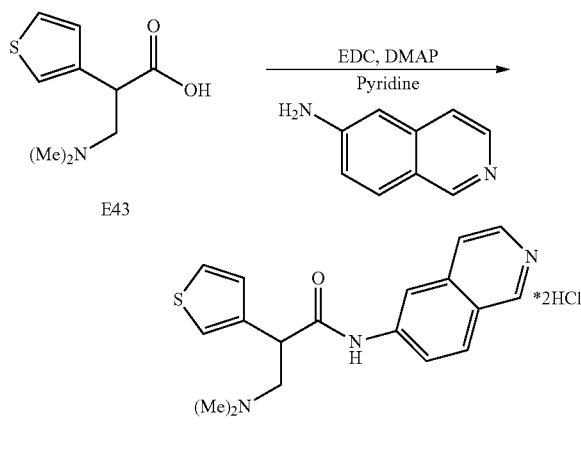

To 3-(dimethylamino)-2-(thiophen-3-yl)propanoic acid (E43) in pyridine was added EDC, DMAP, and 6-aminoisoquinoline. The solution was stirred overnight at room temperature. The mixture was poured into NaHCO$_3$ (sat) and extracted with EtOAc. The organics were dried (Na$_2$SO$_4$), filtered, and evaporated. Column chromatography (SiO$_2$, 5-20% MeOH/CH$_2$Cl$_2$) gave pure 3-(dimethylamino)-N-(isoquinolin-6-yl)-2-(thiophen-3-yl)propanamide. The pure compound was taken up in CH$_2$Cl$_2$ and HCl was added. The solvents were evaporated to give pure 3-(dimethylamino)-N-(isoquinolin-6-yl)-2-(thiophen-3-yl)propanamide dihydrochloride (E44).

Example 45

Preparation of methyl 3-(1,3-dioxoisoindolin-2-yl)-2-(thiophen-3-yl)propanoate (E45)

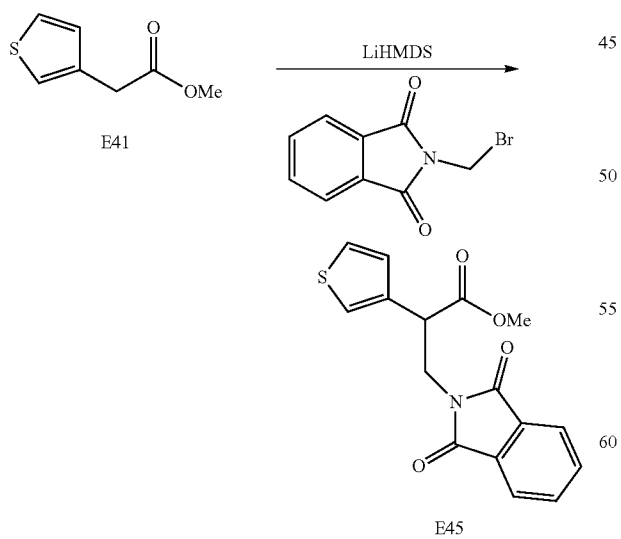

To pure methyl 2-(thiophen-3-yl)acetate (E41) in THF cooled to −78° C. was added LiHMDS, and the solution stirred at −78° C. for 30 min. Then N-(bromomethyl)phthalimide was added directly, and the solution was allowed to warm to 0° C. The mixture was poured into NaHCO$_3$ (sat), extracted with EtOAc, dried (Na$_2$SO$_4$), filtered, and evaporated. Column chromatography (SiO$_2$, 0-40% EtOAc/Hex) gave pure methyl 3-(1,3-dioxoisoindolin-2-yl)-2-(thiophen-3-yl)propanoate (E45).

Example 46

Preparation of 3-amino-2-(thiophen-3-yl)propanoic acid hydrochloride (E46)

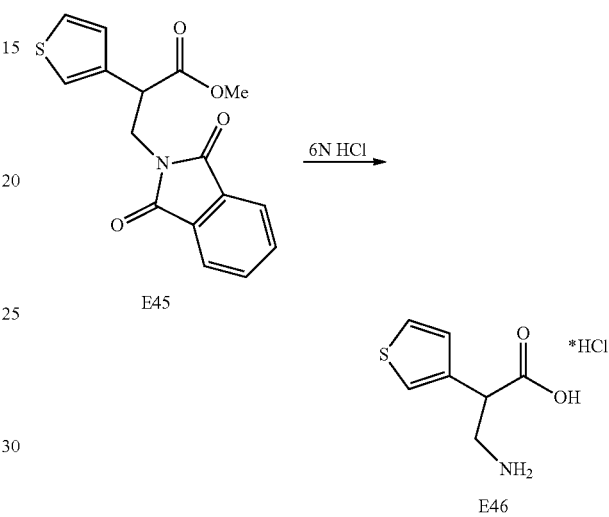

To methyl 3-(1,3-dioxoisoindolin-2-yl)-2-(thiophen-3-yl)propanoate (E45) was added 6 N HCl, and the solution was refluxed for 4 hours. The solvents were evaporated to give 3-amino-2-(thiophen-3-yl)propanoic acid (E46).

Example 47

Preparation of 3-(tert-butoxycarbonylamino)-2-(thiophen-3-yl)propanoic acid (E47)

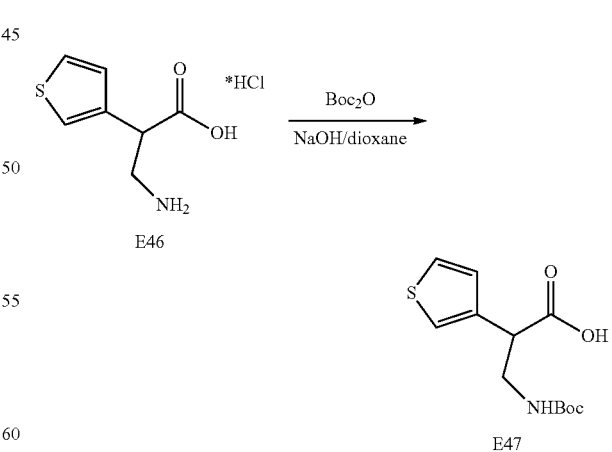

To Boc$_2$O in dioxane at 0° C. was added a cooled solution (0° C.) of 3-amino-2-(thiophen-3-yl)propanoic acid hydrochloride (E46) in 1 N NaOH. The solution was stirred at 0° C. for 30 min, then at room temperature for 4 hours. The mixture was acidified with HCl and extracted with EtOAc and NH$_4$Cl (sat). The organics were dried (Na$_2$SO$_4$), filtered, and evaporated to give pure 3-(tert-butoxycarbonylamino)-2-(thiophen-3-yl)propanoic acid (E47).

Example 48

Preparation of tert-butyl 3-(isoquinolin-6-ylamino)-3-oxo-2-(thiophen-3-yl)propylcarbamate (E48)

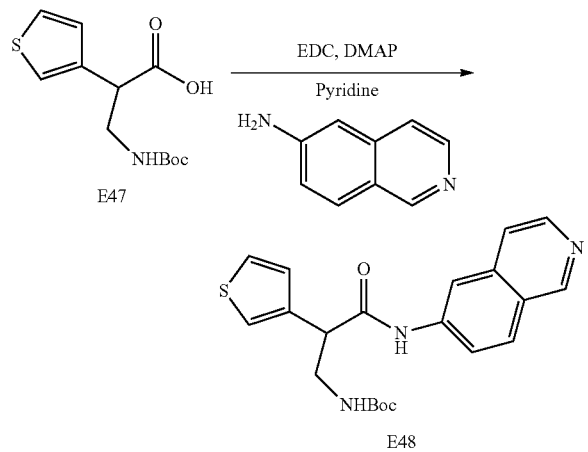

To 3-(tert-butoxycarbonylamino)-2-(thiophen-3-yl)propanoic acid (E47) in pyridine was added EDC, DMAP, and 6-aminoisoquinoline. The solution was stirred overnight at room temperature. The mixture was poured into NaHCO$_3$ (sat) and extracted with EtOAc. The organics were dried (Na$_2$SO$_4$), filtered, and evaporated. Column chromatography (SiO$_2$, 3% MeOH/CH$_2$Cl$_2$) gave pure tert-butyl 3-(isoquinolin-6-ylamino)-3-oxo-2-(thiophen-3-yl) propylcarbamate (E48).

Example 49

Preparation of 3-amino-N-(isoquinolin-6-yl)-2-(thiophen-3-yl)propanamide dihydrochloride (E49)

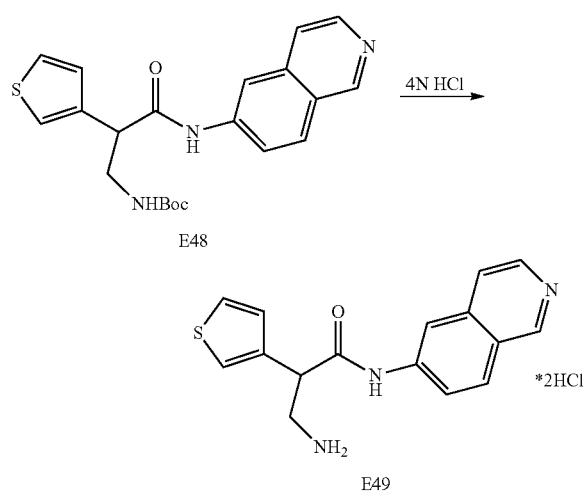

Examples 50-72

To tert-butyl 3-(isoquinolin-6-ylamino)-3-oxo-2-(thiophen-3-yl)propylcarbamate (E48) in CH$_2$Cl$_2$ was added HCl (4N in dioxane), and the solution was stirred for 8-10 hours. The solvents were evaporated to give pure 3-amino-N-(isoquinolin-6-yl)-2-(thiophen-3-yl)propanamide dihydrochloride (E49).

Using commercially available compounds and largely the procedures set forth in Examples 41-49 and substituting the appropriate starting materials, the compounds 50 and 52-54 were made, and compounds 51 and 55-72 can be made.

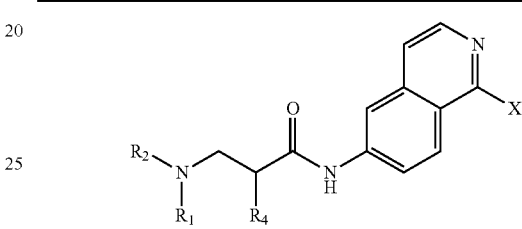

| Example | X | R$_4$ | R$_2$ | R$_1$ |
|---|---|---|---|---|
| 50 | OH | (±)-3-thienyl | Me | Me |
| 51 | OH | (±)-3-thienyl | H | H |
| 52 | H | C$_6$H$_5$ | H | H |
| 53 | H | C$_6$H$_5$ | Me | Me |
| 54 | OH | C$_6$H$_5$ | H | H |
| 55 | OH | C$_6$H$_5$ | Me | Me |
| 56 | H | (±)-2-thienyl | H | H |
| 57 | OH | (±)-2-thienyl | Me | Me |
| 58 | H | (R)—C$_6$H$_5$ | H | H |
| 59 | H | (S)—C$_6$H$_5$ | H | H |
| 60 | OH | p-fluoro-C$_6$H$_4$ | Me | Me |
| 61 | H | p-fluoro-C$_6$H$_4$ | benzyl | H |
| 62 | H | Benzyl | Me | H |
| 63 | H | p-fluoro benzyl | Me | H |
| 64 | OH | 3-pyridyl | H | H |
| 65 | H | 4-pyridyl | Me | Me |
| 66 | OH | 3-furyl | H | H |
| 67 | H | cyclopropyl | Me | Me |
| 68 | H | cyclopentyl | Me | Me |
| 69 | OH | cyclohexyl | H | H |
| 70 | H | 3-benzo[b]thiophene | Me | Me |
| 71 | H | 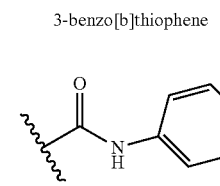 | H | H |
| 72 | OH | 2-oxazole | H | H |

Example 73

Preparation of a Gamma Amino Acid Version. (E73)

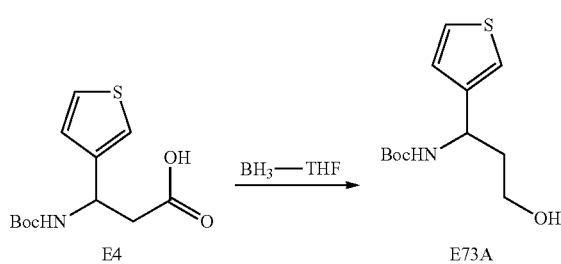

To (±)-2-(tert-butoxycarbonylamino)-2-(thiophen-3-yl) propanoic acid (E4) in THF at 0° C. is added BH$_3$-THF dropwise. The solution is allowed to warm to room temperature and stirred for an additional 2 hours. The solution is cooled to 0° C., quenched with AcOH (10%)/MeOH, and evaporated. Column chromatography (SiO$_2$, EtOAc) gives pure tert-butyl 3-hydroxy-1-(thiophen-3-yl)propylcarbamate (E73A).

Preparation of 3-(tert-butoxycarbonylamino)-3-(thiophen-3-yl)propyl 4-methylbenzenesulfonate (E73B)

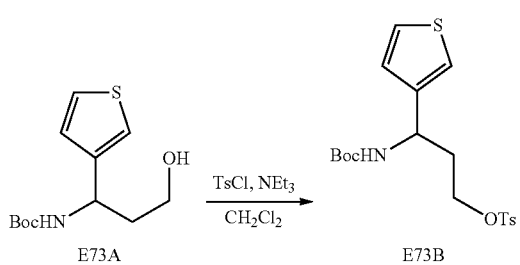

To tert-butyl 2-hydroxy-1-(thiophen-3-yl)ethylcarbamate (E73A) in CH$_2$C$_{12}$ is added NEt$_3$, DMAP, and TsCl. The solution is stirred at room temperature for 3 hours and then poured into NH$_4$Cl (sat) and extracted with EtOAc, dried (Na$_2$SO$_4$), filtered, and evaporated. Column chromatography (SiO$_2$, 30% EtOAc/Hexanes) gives pure 3-(tert-butoxycarbonylamino)-3-(thiophen-3-yl) propyl 4-methylbenzenesulfonate (E73B).

Preparation of tert-butyl 3-cyano-1-(thiophen-3-yl)propylcarbamate (E73C)

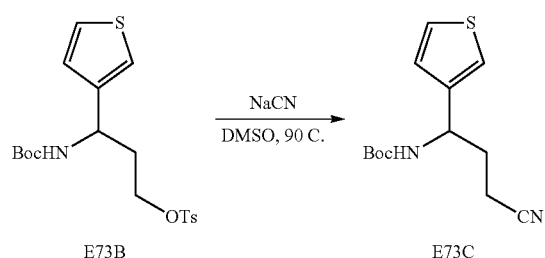 [SMILES: Cc1ccc(S(=O)(=O)OCCC(NC(=O)OC(C)(C)C)c2ccsc2)cc1 ; "NaCN" ; CC(C)(C)OC(=O)NC(CCC#N)c1ccsc1]

To 3-(tert-butoxycarbonylamino)-3-(thiophen-3-yl)propyl 4-methylbenzenesulfonate (E73B) in DMSO is added NaCN, and the solution is heated to 90° C. for 2 hours. The reaction is cooled, poured into NaCl (sat), and extracted with EtOAc. The organics are dried (Na$_2$SO$_4$), filtered, and evaporated. Column chromatography (SiO$_2$, 25% EtOAc/Hexanes) gives pure tert-butyl 2-cyano-1-(thiophen-3-yl)ethylcarbamate (E73C).

Preparation of 3-(tert-butyoxcarbonylamino)-3-(thiophen-3-yl)propanoic acid (E73D)

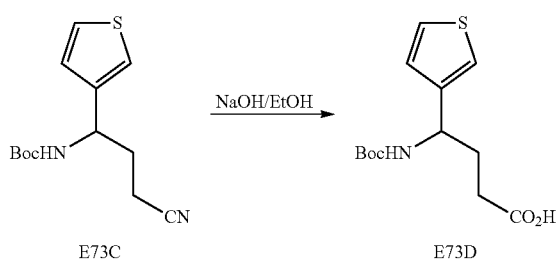 [SMILES: CC(C)(C)OC(=O)NC(CCC#N)c1ccsc1 ; "NaOH/EtOH" ; CC(C)(C)OC(=O)NC(CCC(=O)O)c1ccsc1]

To tert-butyl 3-cyano-1-(thiophen-3-yl)propylcarbamate (E3) in EtOH is added NaOH (2M) and the solution is heated to 90° C. for 4 hours. The reaction is cooled, acidified with HCl, and extracted with EtOAc. The organics are dried (Na$_2$SO$_4$) and evaporated to give pure 4-(tert-butyoxcarbonylamino)-4-(thiophen-3-yl)butanoic acid (E73D).

Preparation of tert-butyl 4-(isoquinolin-6-ylamino)-4-oxo-1-(thiophen-3-yl)butylcarbamate (E73E)

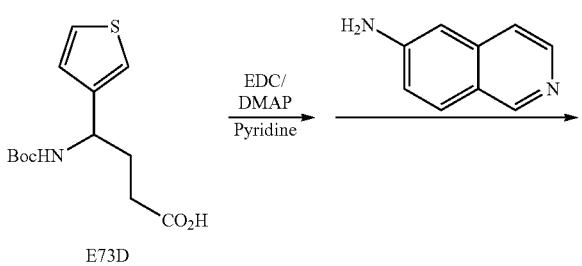

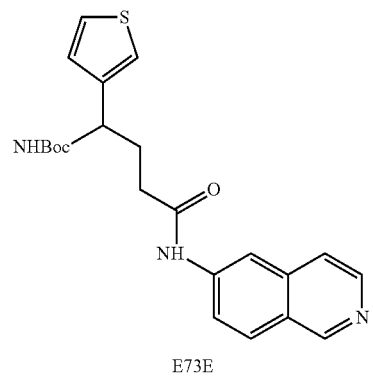

To 4-(tert-butyoxcarbonylamino)-4-(thiophen-3-yl)butanoic acid (E73D) in pyridine is added EDC, DMAP and 6-aminoisoquinoline and the solution is stirred for 10 hours at room temperature. The mixture is poured into NaHCO$_3$ (sat) and extracted with EtOAc, dried (Na$_2$SO$_4$), filtered and evaporated. Column chromatography (SiO$_2$, 5% MeOH/

CH$_2$Cl$_2$) gives pure tert-butyl 4-(isoquinolin-6-ylamino)-4-oxo-1-(thiophen-3-yl)butylcarbamate (E73E).

Preparation of 4-amino-N-(isoquinolin-6-yl)-4-(thiophen-3-yl)butanamide dihydrochloride (E73)

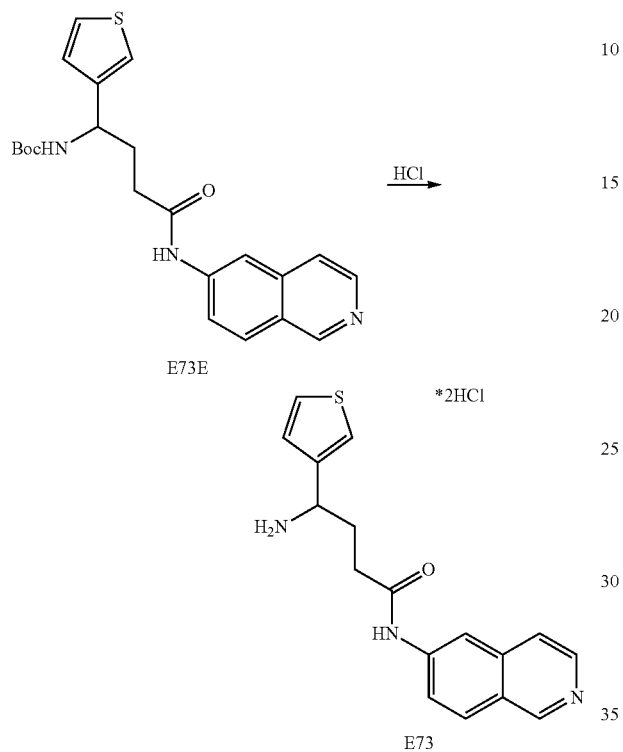

To tert-butyl 4-(isoquinolin-6-ylamino)-4-oxo-1-(thiophen-3-yl)butylcarbamate (E73E) in CH$_2$Cl$_2$ is added HCl (4N in dioxane), and the solution is stirred for 8 hours. The solvents are evaporated to give 4-amino-N-(isoquinolin-6-yl)-4-(thiophen-3-yl)butanamide dihydrochloride (E73).

Examples 74-93

Using the general procedure shown for Example 73, the following compounds 74-93 can be synthesized from the corresponding 6-aminoisoquinoline.

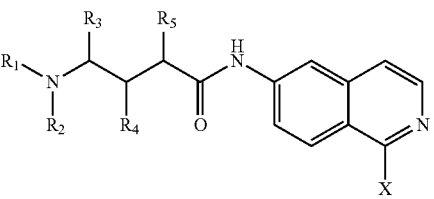

| Example | X | R5 | R4 | R3 | R2 | R1 |
|---|---|---|---|---|---|---|
| 74 | H | C$_6$H$_5$ | H | H | H | H |
| 75 | OH | C$_6$H$_5$ | H | H | H | H |
| 76 | H | (S)—C$_6$H$_5$ | H | H | H | H |
| 77 | OH | (R)—C$_6$H$_5$ | H | H | H | H |
| 78 | OH | (S)—C$_6$H$_5$ | H | H | H | H |
| 79 | H | (S)—C$_6$H$_5$ | H | H | CH$_3$ | CH$_3$ |
| 80 | H | p-fluoro-C$_6$H$_4$ | H | H | H | H |
| 81 | H | p-fluoro-C$_6$H$_4$ | H | H | CH$_3$ | H |
| 82 | OH | cyclopropyl | H | H | CH$_3$ | H |
| 83 | H | 3-thienyl | H | H | H | H |
| 84 | H | (S)-3-thienyl | H | H | H | H |
| 85 | OH | cyclohexyl | H | H | CH$_3$ | CH$_3$ |
| 86 | H | H | C$_6$H$_5$ | H | H | H |
| 87 | H | H | C$_6$H$_5$ | H | CH$_3$ | H |
| 88 | H | C$_6$H$_5$ | H | H | CH$_2$C$_6$H$_5$ | H |
| 89 | H | H | p-fluoro-C$_6$H$_4$ | H | H | H |
| 90 | OH | H | CH$_2$C$_6$H$_5$ | H | CH$_3$ | H |
| 91 | H | H | 3-thienyl | H | CH$_3$ | H |
| 92 | OH | H | 2-thienyl | H | CH$_3$ | CH$_3$ |
| 93 | H | H | p-chlorobenzyl | H | H | H |

Examples 94-110

Using largely the procedure set forth in Example 73 and substituting the appropriate starting materials, the compounds 94-110 can be made.

94

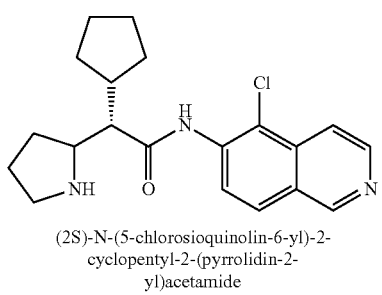

(2S)-N-(5-chlorosioquinolin-6-yl)-2-cyclopentyl-2-(pyrrolidin-2-yl)acetamide

95

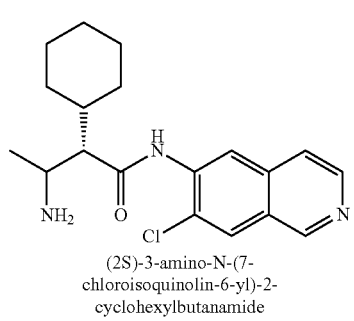

(2S)-3-amino-N-(7-chloroisoquinolin-6-yl)-2-cyclohexylbutanamide

-continued

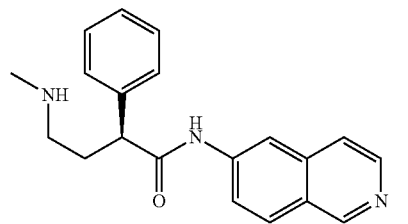

(S)-N-(isoquinolin-6-yl)-4-
(methylamino)-2-
phenylbutanamide

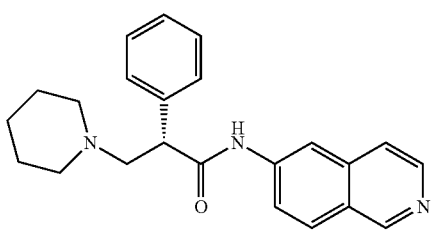

(S)-N-(isoquinolin-6-yl)-2-
phenyl-3-(piperidin-1-
yl)propanamide

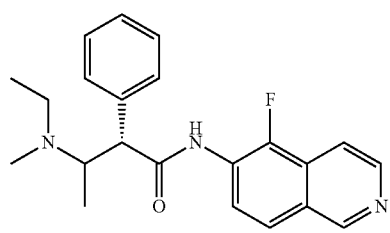

(2S-3-(ethyl(methyl)amino)-N-
(5-fluoroisoquinolin-6-yl)-2-
phenylbutanamide

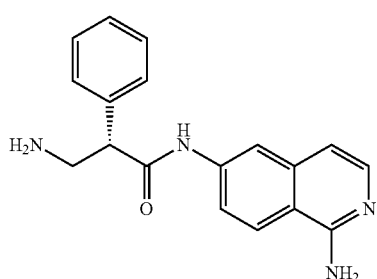

(S)-3-amino-N-(1-aminoisoquinolin-
6-yl)-2-phenylpropanamide

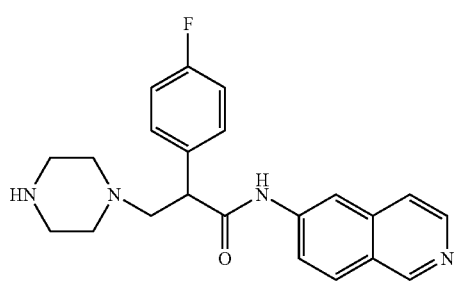

2-(4-fluorophenyl)-N-(isoquinolin-6-yl)-
3-(piperazin-1-yl)propanamide

-continued

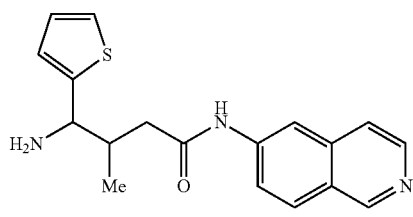

4-amino-N-(isoquinolin-6-yl)-3-
methyl-4-(thiophen-2-yl)butanamide

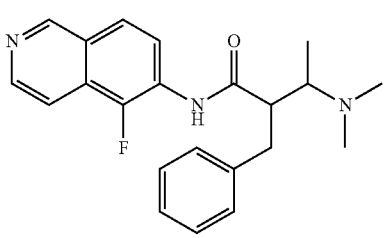

2-benzyl-3-(dimethylamino)-N-
(5-fluoroisoquinolin-6-
yl)-butanamide

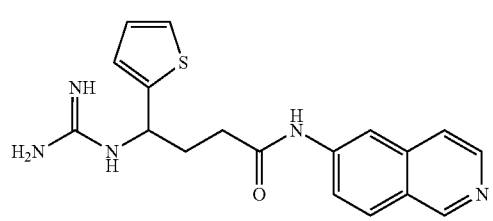

4-guanidino-N-(isoquinolin-6-yl)-4-
(thiophen-2-yl)butanamide

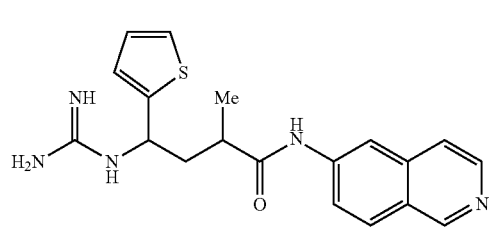

4-guinidino-N-(isoquinolin-6-yl)-2-
methyl-4-(thiophen-2-yl)butanamide

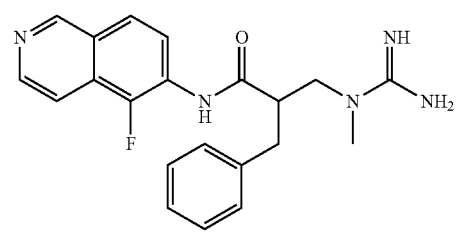

2-benzyl-N-(5-fluoroisoquinolin-6-
yl)-3-(1-
methylguanidino)propanamide

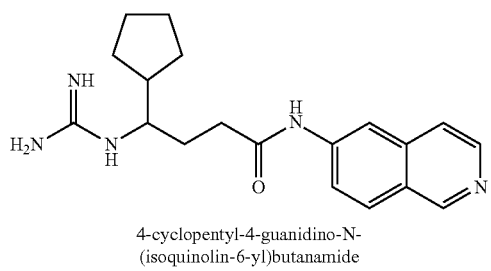

4-cyclopentyl-4-guanidino-N-(isoquinolin-6-yl)butanamide

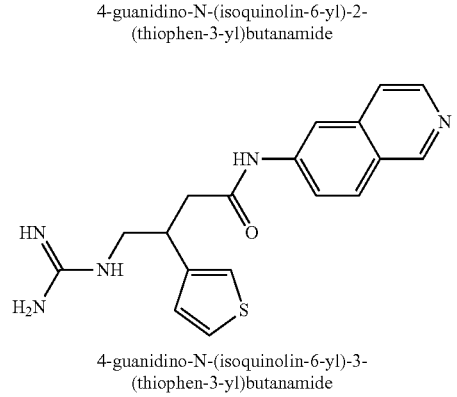

4-guanidino-N-(isoquinolin-6-yl)-2-(thiophen-3-yl)butanamide 4-guanidino-N-(isoquinolin-6-yl)-3-(thiophen-3-yl)butanamide

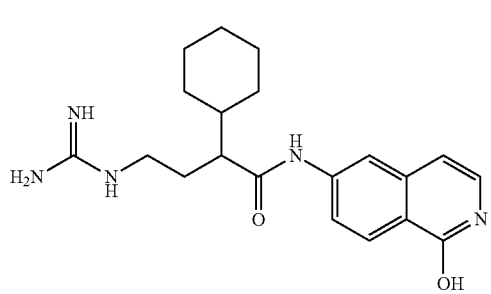

4-guanidino-N-(1-hydroxyisoquinolin-6-yl)-4-(thiophen-2-yl)butanamide 2-cyclohexyl-4-guanidino-N-(1-hydroxyisoquinolin-6-yl)butanamide

Example 111

Preparation of 2-methyl-4-nitrobenzamide (E111)

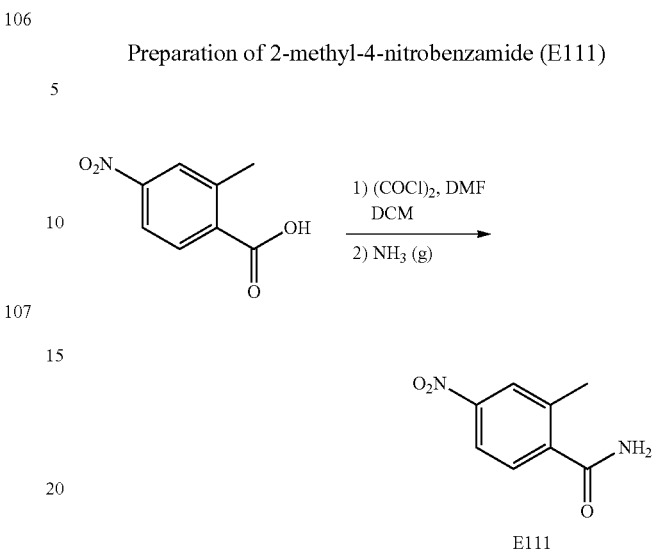

To 2-methyl-4-nitrobenzoic acid suspended in $CH_2Cl_2$ under Ar was added DMF then oxalyl chloride. The reaction was stirred at room temperature 1.5 hours then the solvent was evaporated. The residue was dissolved in THF and ammonia gas was bubbled through the reaction for 15 minutes. The solvent was evaporated and the residue partitioned between EtOAc and water. The aqueous layer was extracted with EtOAc. The extracts were dried ($MgSO_4$), filtered and evaporated. Column chromatography ($SiO_2$, 0-100% EtOAc/Hex) gave pure 2-methyl-4-nitrobenzamide (E111).

Example 112

Preparation of 4-amino-2-methylbenzamide (E112)

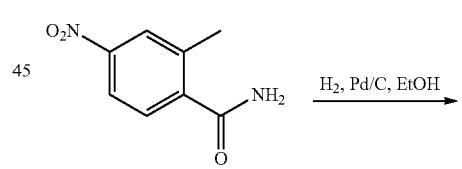

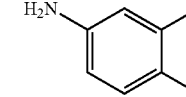

2-methyl-4-nitrobenzamide (E111) was dissolved in EtOH under Ar and 10% Pd/C added. The reaction was pump-purged with $H_2$ and left stirring at room temperature overnight. The catalyst was removed by filtration and the reaction concentrated to give pure 4-amino-2-methylbenzamide (E112).

Example 113

Preparation of 4-(2-(dimethylamino)-2-(thiophen-3-yl)acetamido)-2-methylbenzamide (E113)

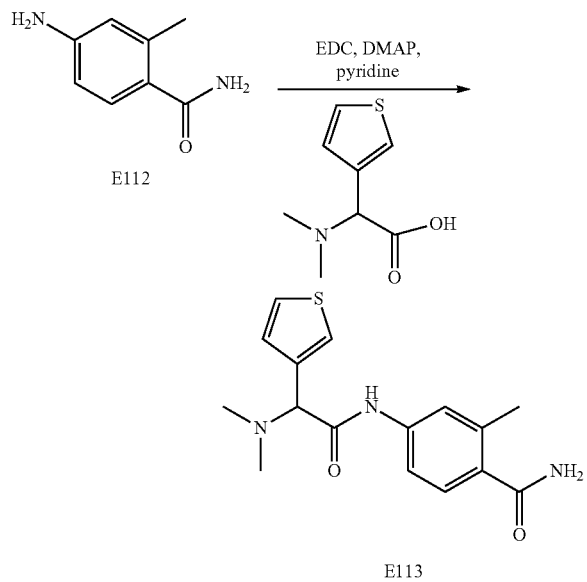

To 2-(dimethylamino)-2-(thiophen-3-yl)acetic acid in pyridine was added EDC, DMAP and 4-amino-2-methylbenzamide (E112) and the solution was stirred for 10 hours at room temperature. The mixture was poured into NaHCO₃ (sat) and extracted with EtOAc. The extracts were dried (MgSO₄), filtered and evaporated. Column chromatography (SiO₂, 0-100% EtOAc/Hex) gave pure 4-(2-(dimethylamino)-2-(thiophen-3-yl)acetamido)-2-methylbenzamide (E113).

Example 114

Preparation of methyl 4-(2-(dimethylamino)-2-(thiophen-3-yl)acetamido)benzoate (E114)

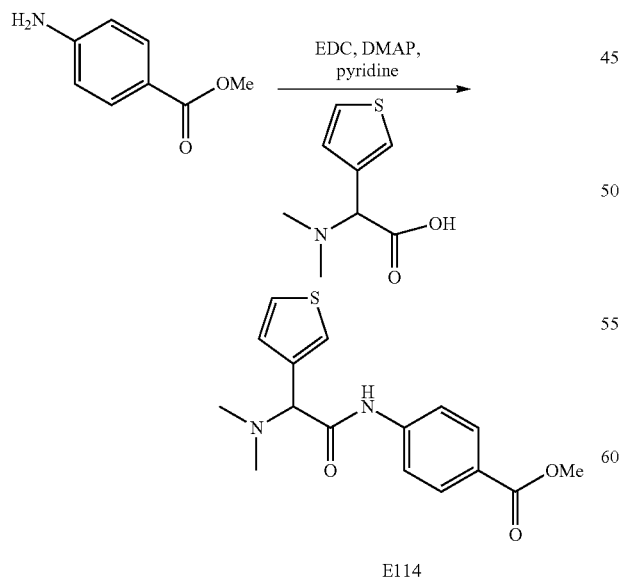

To 2-(dimethylamino)-2-(thiophen-3-yl)acetic acid in pyridine was added EDC, DMAP and 4-aminobenzoate and the solution was stirred for 10 hours at room temperature. The mixture was poured into NaHCO₃ (sat) and extracted with EtOAc. The extracts were dried (MgSO₄), filtered and evaporated. Column chromatography (SiO₂, 0-100% EtOAc/Hex) gave pure methyl 4-(2-(dimethylamino)-2-(thiophen-3-yl)acetamido)benzoate (E114).

Example 115

Preparation of 4-(2-(dimethylamino)-2-(thiophen-3-yl)acetamido)benzamide (E115)

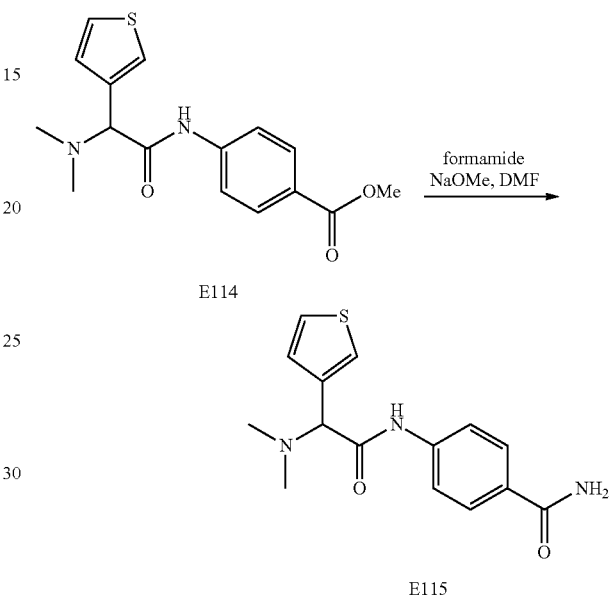

Methyl 4-(2-(dimethylamino)-2-(thiophen-3-yl)acetamido)benzoate (E114) and formamide dissolved in DMF under Ar were heated to 100° C. The NaOMe was then added and the reaction heated for 2 hours. The reaction was partitioned between EtOAc and water. The aqueous layer was extracted with EtOAc. The extracts were dried (MgSO₄), filtered and evaporated. Column chromatography (SiO₂, 0-100% EtOAc/Hex) gave pure 4-(2-(dimethylamino)-2-(thiophen-3-yl)acetamido)benzamide (E115).

Examples 116-122

Using commercially available compounds and largely the procedures set forth in Examples 111-115 and substituting the appropriate starting materials, the compounds 116-122 were made:

| Example | R1 | R2 |
|---|---|---|
| 116 | H | H |
| 117 | Cl | H |

| | | |
|---|---|---|
| 118 | Cl | CH₃ |
| 119 | H | C₆H₅ |
| 120 | H | CH₃ |

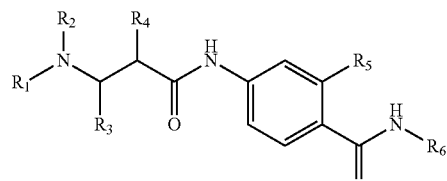

| Example | R6 | R5 | R4 | R3 | R2 | R1 |
|---|---|---|---|---|---|---|
| 121 | H | H | H | (S)—C₆H₅ | H | H |
| 122 | H | H | C₆H₅ | H | H | H |

Examples 123-133

Using commercially available compounds and largely the procedures set forth in Examples 111-115 and substituting the appropriate starting materials, the compounds 125 and 127 were made, and compounds 123-124, 126, and 128-133 can be made.

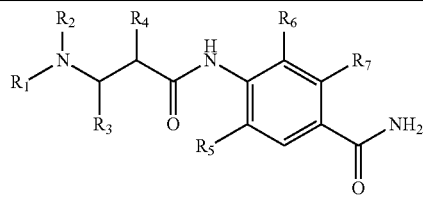

| Example | R1 | R2 | R3 | R4 |
|---|---|---|---|---|
| 123 | F | H | H | H |
| 124 | Cl | H | H | H |
| 125 | H | H | —OMe | H |
| 126 | Cl | Cl | H | H |
| 127 | —OMe | H | H | H |
| 128 | H | H | F | H |
| 129 | CH₃ | CH₃ | H | H |
| 130 | CH₃ | H | H | H |
| 131 | H | H | H | OMe |
| 132 | H | H | H | OH |
| 133 | H | H | H | NH₂ |

Examples 134-180

Using commercially available compounds and largely the procedures set forth in Examples 111-115 and substituting the appropriate starting materials, the compounds 134-180 can be made:

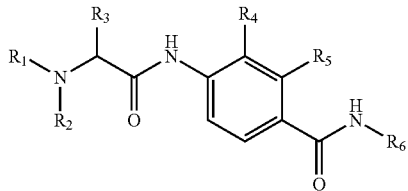

| Example | R1 | R2 | R3 | R4 | R5 | R6 |
|---|---|---|---|---|---|---|
| 134 | H | H | 3-thienyl | Cl | Cl | H |
| 135 | H | H | 3-thienyl | H | H | H |
| 136 | H | H | 3-thienyl | F | F | H |
| 137 | H | H | C₆H₆ | H | H | H |
| 138 | CH₃ | CH₃ | C₆H₆ | H | H | H |
| 139 | CH₃ | CH₃ | C₆H₆ | F | Cl | H |
| 140 | CH₃ | CH₃ | cyclohexyl | H | H | H |
| 141 | CH₃ | CH₃ | —CH(CH₃)₂ | H | H | H |
| 142 | CH₃ | CH₃ | 3-thienyl | CF₃ | H | H |
| 143 | CH₃ | CH₃ | 3-thienyl | OCF₃ | H | H |
| 144 | CH₃ | CH₃ | 3-thienyl | CN | H | H |
| 145 | CH₃ | CH₃ | 2-pyridyl | H | H | H |
| 146 | CH₃ | CH₃ | 3-pyridyl | H | H | H |
| 147 | CH₃ | CH₃ | 4-pyridyl | H | H | H |
| 148 | CH₃ | CH₃ | 2-thienyl | H | H | H |
| 149 | H | CH₃ | 3-thienyl | H | H | H |
| 150 | CH₃ | CH₃ | 3-thienyl | NO₂ | H | H |

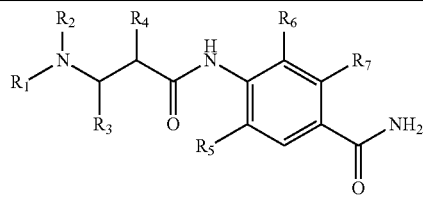

| Example | R1 | R2 | R3 | R4 | R5 | R6 | R7 |
|---|---|---|---|---|---|---|---|
| 151 | H | H | 3-thienyl | H | H | H | H |
| 152 | CH₃ | CH₃ | 3-thienyl | H | H | H | H |
| 153 | H | H | H | 3-thienyl | H | H | H |
| 154 | CH₃ | CH₃ | H | 3-thienyl | H | H | H |
| 155 | CH₃ | CH₃ | 3-thienyl | H | F | H | H |
| 156 | CH₃ | CH₃ | 3-thienyl | H | H | F | H |
| 157 | CH₃ | CH₃ | 3-thienyl | H | H | H | F |
| 158 | CH₃ | CH₃ | H | 3-thienyl | CH₃ | H | H |
| 159 | CH₃ | CH₃ | H | 3-thienyl | H | CH₃ | H |
| 160 | CH₃ | CH₃ | H | 3-thienyl | H | H | CH₃ |
| 161 | CH₃ | CH₃ | C₆H₅ | H | H | H | H |
| 162 | H | H | cyclohexyl | H | H | H | H |
| 163 | CH₃ | H | —CH(CH₃)₂ | H | H | H | H |
| 164 | CH₃ | CH₃ | H | C₆H₆ | H | H | H |
| 165 | CH₃ | H | H | cyclohexyl | H | H | H |
| 166 | H | H | H | —CH(CH₃)₂ | H | H | H |
| 167 | CH₃ | CH₃ | —C≡C—C₆H₅ | H | H | H | H |
| 168 | CH₃ | CH₃ | 3-thienyl | H | Cl | Cl | H |

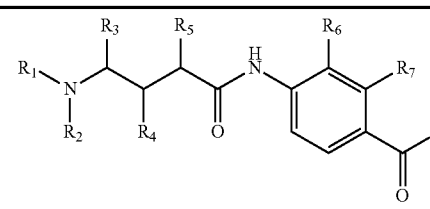

| Example | R1 | R2 | R3 | R4 | R5 | R6 | R7 |
|---|---|---|---|---|---|---|---|
| 169 | H | H | 3-thienyl | H | H | H | H |
| 170 | CH₃ | CH₃ | 3-thienyl | H | H | H | H |

-continued

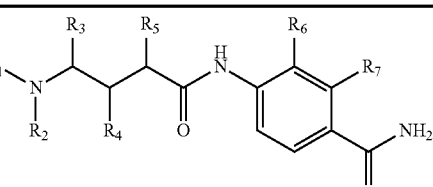

| Example | R1 | R2 | R3 | R4 | R5 | R6 | R7 |
|---|---|---|---|---|---|---|---|
| 171 | H | H | H | 3-thienyl | H | H | H |
| 172 | CH₃ | CH₃ | H | 3-thienyl | H | H | H |
| 173 | CH₃ | CH₃ | H | H | 3-thienyl | H | H |
| 174 | CH₃ | CH₃ | H | H | 3-thienyl | F | H |
| 175 | H | H | cyclohexyl | H | H | H | F |
| 176 | H | H | H | —CH(CH3)2 | H | H | H |
| 177 | H | H | H | H | C₆H₅ | CH₃ | H |
| 178 | CH₃ | CH₃ | H | cyclopropyl | H | H | CH₃ |
| 179 | CH₃ | CH₃ | C₆H₅ | H | H | H | H |
| 180 | H | H | H | 4-pyridyl | H | H | H |

Example 181

Using commercially available compounds and largely the procedures set forth in Examples 1-6 and substituting the appropriate starting materials, the compounds 181-195 were made.

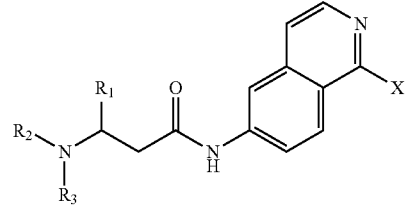

| Example | X | R₁ | R₂ | R₃ |
|---|---|---|---|---|
| 181 | H | (S)—C₆H₅ | Me | Me |
| 182 | H | (R)-3-thienyl | H | H |
| 183 | OH | (R)-3-thienyl | H | H |
| 184 | H | (S)-2-thienyl | H | H |
| 185 | OH | (S)-2-thienyl | H | H |
| 186 | OH | (S)-2-thienyl | Me | Me |
| 187 | H | (R)—CH₂-3-thienyl | H | H |
| 188 | H | (S)—CH₂-2-thienyl | H | H |
| 189 | H | (S)-2-furyl | H | H |
| 190 | H | (S)-3-pyridyl | H | H |
| 191 | H | (S)-2-methoxy-5-pyridyl | H | H |

192

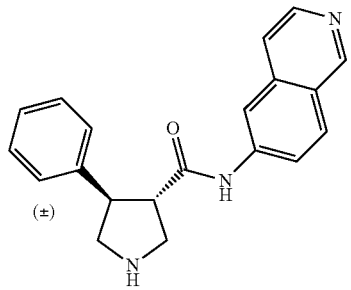

(trans)-N-(isoquinolin-6-yl)-4-phenylpyrrolidine-3-carboxamide

-continued

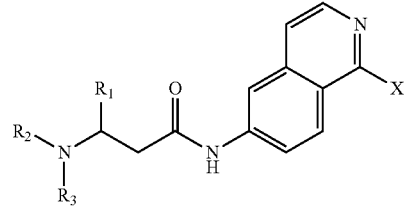

| Example | X | R₁ | R₂ | R₃ |
|---|---|---|---|---|

193

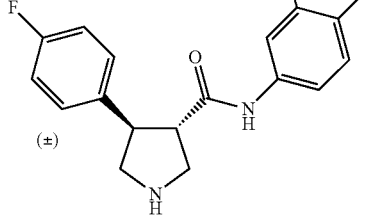

(trans)-4-(4-fluorophenyl)-N-(isoquinolin-6-yl)pyrrolidine-3-carboxamide

194

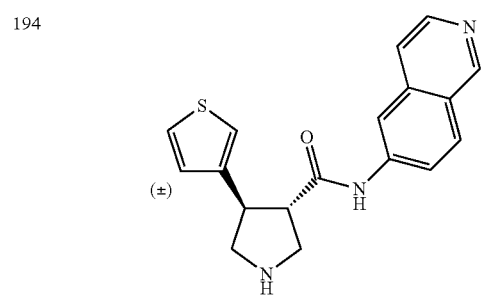

(trans)-N-(isoquinolin-6-yl)-4-(thiophen-3-yl)pyrrolidine-3-carboxamide

195

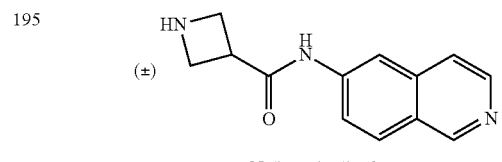

N-(isoquinolin-6-yl)azetidine-3-carboxamide

Example 182

Using commercially available compounds and largely the procedures set forth in Examples 41-49 and substituting the appropriate starting materials, the compounds 196-202 were made.

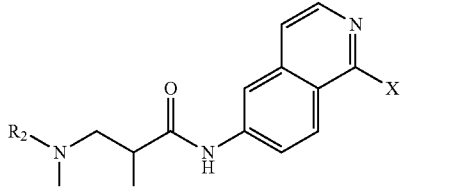

| Example | X | R₁ | R₂ | R₃ |
|---|---|---|---|---|
| 196 | H | (±)-3-thienyl | H | H |
| 197 | H | (±)-3-thienyl | Me | Me |
| 198 | H | C₆H₅ | Me | H |
| 199 | H | 4-fluoro-C₆H₄ | H | H |

200

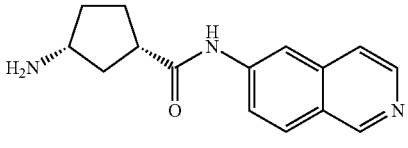

3-guanidino-N-(isoquinolin-6-yl)-2-phenylpropanamide

201

(1S,3R)-3-amino-N-(isoquinolin-6-yl)cyclopentanecarboxamide

202

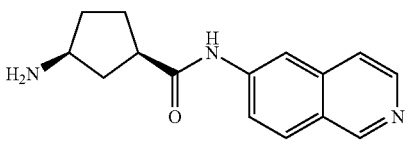

(1R,3S)-3-amino-N-(isoquinolin-6-yl)cyclopentanecarboxamide

Example 183

Topical pharmaceutical compositions for lowering intraocular pressure are prepared by conventional methods and formulated as follows:

| Ingredient | Amount (wt %) |
|---|---|
| beta amino acid isoquinolyl amide | 0.50 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 5.5-6.5 |
| Purified water | q.s. to 100% |

A compound according to this invention is used as the beta amino acid isoquinolyl amide. When the composition is topically administered to the eyes once daily, the above composition decreases intraocular pressure in a subject suffering from glaucoma.

Example 184

Example 183 is repeated using 3-amino-N-(isoquinolin-6-yl)-3-(thiophen-3-yl)propanamide dihydrochloride (E6) according to this invention. When administered as a drop 2 times per day, the above composition decreases intraocular pressure and serves as a neuroprotective agent.

Example 185

Example 183 is repeated using a gamma amino acid isoquinolyl amide according to this invention. When administered as a drop twice per day, the above composition decreases intraocular pressure.

Example 186

Example 183 is repeated using a benzamide according to this invention. When administered as a drop twice per day, the above composition substantially decreases allergic symptoms and relieves dry eye syndrome.

Example 187

Example 183 is repeated using 3-(dimethylamino)-N-(isoquinolin-6-yl)-2-(thiophen-3-yl)propanamide dihydrochloride (E44) according to this invention. When administered as a drop as needed, the above composition decreases hyperemia, redness and ocular irritation.

Example 188

Example 183 is repeated using 3-amino-N-(5-chloroisoquinolin-6-yl)-2-(thiophen-3-yl)propanamide dihydrochloride according to this invention. When administered as a drop 4 times per day, the above composition decreases intraocular pressure and serves as a neuroprotective agent.

Example 189

Example 183 is repeated using 3-amino-N-(isoquinolin-6-yl)-2-(thiophen-3-yl)propanamide dihydrochloride (E49) according to this invention. When administered as a drop twice per day, the above composition decreases intraocular pressure.

Example 190

Example 183 is repeated using 4-(2-(dimethylamino)-2-(thiophen-3-yl) acetamido)benzamide (E115) according to this invention. When administered as a drop twice per day, the above composition decreases ocular pressure, allergic symptoms and relieves dry eye syndrome.

Reference Example One

The Cell-Based Porcine Trabecular Meshwork (PTM) Assay

The anterior section of porcine eyes was harvested within 4 hours post-mortem. The iris and ciliary body were removed and trabecular meshwork cells were harvested by blunt dissection. Finely minced trabecular meshwork tissue was plated into collagen-coated 6-well plates in Medium-199 containing 20% fetal bovine serum (FBS). After two passages at confluence, cells were transferred to low-glucose DMEM containing 10% FBS. Cells were used between passage 3 and passage 8.

Cells were plated into fibronectin-coated, glass multiwell plates the day before compound testing under standard culture conditions. Compounds were added to cells in the presence of 1% FBS-containing DMEM and 1% DMSO. When compounds were incubated with the cells for the duration determined to be optimal, the media and compound is removed and cells fixed for 20 minutes in 3% methanol-free paraformaldehyde. Cells were rinsed twice with phosphate buffered saline (PBS) and cells are permeabilized with 0.5% Triton X-100 for two minutes. Following an additional two washes with PBS, F-actin was stained with Alexa-fluor 488-labelled phalloidin and nuclei are stained with DAPI.

Data was reduced to the mean straight actin-fiber length and normalized to DMSO-treated control cells (100%) and 50 μM Y-27632 (0%). Y-27632 is a rho-kinase inhibitor known to result in the depolymerization of F-actin in these cells.

Reference Example Two

Pharmacological Activity for Glaucoma Assay

Pharmacological activity for glaucoma can be demonstrated using assays designed to test the ability of the subject compounds to decrease intraocular pressure. Examples of such assays are described in the following reference, incorporated herein by reference: C. Liljebris, G. Selen, B. Resul, J. Sternschantz, and U. Hacksell, "Derivatives of 17-phenyl-18,19,20-trinorprostaglandin $F_{2\alpha}$ Isopropyl Ester: Potential Anti-glaucoma Agents", *Journal of Medicinal Chemistry* 1995, 38 (2): 289-304.

While the invention has been described in detail and with reference to specific embodiments thereof, it will be apparent to one skilled in the art that various changes and modifications can be made without departing from the spirit and scope of the invention.

What is claimed is:

1. A compound of formula (I):

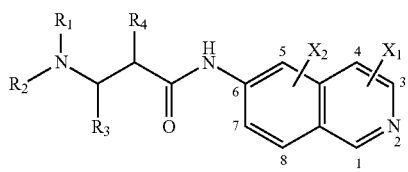

or any optical isomer, diastereomer, enantiomer, tautomer, or physiologically acceptable salt thereof;
wherein $R_1$ and $R_2$ are, independently, hydrogen, $C_1$-$C_4$ alkyl, $C_2$-$C_4$ alkenyl, $C_1$-$C_4$ carbonyl, or $C_1$-$C_4$ carboxyl; or $R_1$ and $R_2$ combine to form a heterocycloalkyl ring of at least 5 and at most 8 member atoms, or $R_1$ and $R_3$ combine to form a heterocycloalkyl ring of at least 5 and at most 8 member atoms;
wherein one of $R_3$ and $R_4$ is an aryl group, a heteroaryl group, a cycloalkyl group, a heterocycloalkyl group, $C_1$-$C_8$ alkenyl, and the other of $R_3$ and $R_4$ is hydrogen or $C_1$-$C_4$ alkyl; and
wherein $X_1$ and $X_2$ are, independently, hydrogen, hydroxyl, halogen, $C_1$-$C_4$ alkyl, $C_2$-$C_4$ alkenyl, amino, nitro, or cyano.

2. The compound according to claim 1, wherein one of $R_3$ and $R_4$ is aryl or heteroaryl.

3. The compound according to claim 2, wherein $R_1$ and $R_2$ are, independently, hydrogen or methyl.

4. The compound according to claim 1, wherein $X_1$ and $X_2$ are, independently, hydrogen, hydroxy, chloro or fluoro.

5. The compound according to claim 1, wherein one of $R_3$ and $R_4$ is aryl or heteroaryl; wherein $R_1$ and $R_2$ are, independently, hydrogen or methyl; and wherein $X_1$ and $X_2$ are, independently, hydrogen, hydroxyl, chloro or fluoro.

6. The compound according to claim 5, wherein the other of $R_3$ and $R_4$ is hydrogen.

7. The compound according to claim 1, wherein one of $R_3$ and $R_4$ is aryl or heteroaryl.

8. The compound according to claim 2, wherein one of $R_3$ and $R_4$ is thienyl.

9. The compound according to claim 2, wherein one of $R_3$ and $R_4$ is monosubstituted phenyl or monosubstituted thienyl.

10. The compound according to claim 9, wherein the substituent is fluoro, chloro or cyano.

11. The compound according to claim 2, wherein one of $R_3$ and $R_4$ is unsubstituted phenyl or unsubstituted thienyl.

12. The compound according to claim 1, wherein $X_1$ is hydroxy and $X_2$ is hydrogen.

13. The compound according to claim 1, wherein a hydroxy is at the 1-position.

14. The compound according to claim 1, wherein a hydrogen is at the 1-position.

15. The compound according to claim 1, wherein $R_1$ and $R_2$ are, independently, hydrogen or methyl; $R_3$ is hydrogen, $R_4$ is phenyl; $X_1$ and $X_2$ are hydrogen.

16. A compound of formula (II):

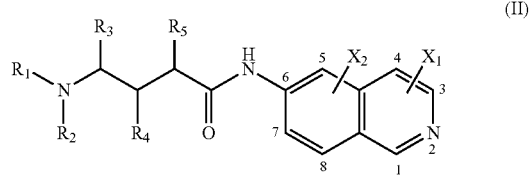

or any optical isomer, diastereomer, enantiomer, tautomer, or physiologically acceptable salt thereof;
wherein $R_1$ and $R_2$ are, independently, hydrogen, $C_1$-$C_4$ alkyl, $C_2$-$C_4$ alkenyl, $C_1$-$C_4$ carbonyl, or $C_1$-$C_4$ carboxyl; or $R_1$ and $R_2$ combine to form a heterocycloalkyl ring of at least 5 and at most 8 member atoms, or $R_1$ and $R_3$ combine to form a heterocycloalkyl ring of at least 5 and at most 8 member atoms;
wherein one of $R_3$, $R_4$, and $R_5$ is an aryl group, a heteroaryl group, a cycloalkyl group, a heterocycloalkyl group, $C_1$-$C_8$ alkyl, or $C_2$-$C_8$ alkenyl, and the other two of $R_3$, $R_4$, and $R_5$ is hydrogen or $C_1$-$C_4$ alkyl; and
wherein $X_1$ and $X_2$ are, independently, hydrogen, hydroxyl, halogen, $C_1$-$C_4$ alkyl, $C_2$-$C_4$ alkenyl, amino, nitro, or cyano.

17. The compound according to claim 16, wherein one of $R_3$, $R_4$ and $R_5$ is aryl or heteroaryl.

18. The compound according to claim 17, wherein $R_1$ and $R_2$ are, independently, hydrogen or methyl.

19. The compound according to claim 16, wherein $X_1$ and $X_2$ are, independently, hydrogen, hydroxy, chloro or fluoro.

20. The compound according to claim 16, wherein one of $R_3$, $R_4$ and $R_5$ is aryl or heteroaryl; wherein $R_1$ and $R_2$ are, independently, hydrogen or methyl; and wherein $X_1$ and $X_2$ are, independently, hydrogen, hydroxyl, chloro or fluoro.

21. The compound according to claim 20, wherein the other of $R_3$, $R_4$ and $R_5$ are hydrogen.

22. The compound according to claim 16, wherein one of $R_3$, $R_4$ and $R_5$ is aryl or heteroaryl.

23. The compound according to claim 22, wherein one of $R_3$, $R_4$ and $R_5$ is thienyl.

24. The compound according to claim 22, wherein one of $R_3$, $R_4$ and $R_5$ is monosubstituted phenyl or monosubstituted thienyl.

25. The compound according to claim 24, wherein the substituent is fluoro, chloro or cyano.

26. The compound according to claim 24, wherein one of $R_3$, $R_4$ and $R_5$ is unsubstituted phenyl or unsubstituted thienyl.

27. The compound according to claim 16, wherein $X_1$ is hydroxy and $X_2$ is hydrogen.

28. The compound according to claim 16, wherein a hydroxy is at the 1-position.

29. The compound according to claim 16, wherein a hydrogen is at the 1-position.

30. The compound according to claim 16, wherein $R_1$ and $R_2$ are, independently, hydrogen or methyl; $R_3$ and $R_4$ are hydrogen, $R_5$ is phenyl; $X_1$ and $X_2$ are hydrogen.

31. A composition comprising a compound according to claim 1 and a carrier.

32. The composition of claim 31, wherein the carrier is saline buffered to a pH of about 5.5 to about 6.5.

33. A composition comprising a compound according to claim 16 and a carrier.

34. The composition of claim 33, wherein the carrier is saline buffered to a pH of about 5.5 to about 6.5.

35. A method of treating a disease in a subject comprising:
administering to a subject an effective amount of a compound according to claim 1;
wherein the disease comprises eye disease.

36. The method of claim 35, wherein the eye disease comprises glaucoma or a neurodegenerative eye disease.

* * * * *